US010335298B2

(12) United States Patent
Armstrong et al.

(10) Patent No.: US 10,335,298 B2
(45) Date of Patent: Jul. 2, 2019

(54) STENT

(71) Applicant: W. L. Gore & Associates, Inc., Newark, DE (US)

(72) Inventors: Joseph R. Armstrong, Flagstaff, AZ (US); Edward H. Cully, Flagstaff, AZ (US); Michael W. Franklin, Flagstaff, AZ (US); Mark Y. Hansen, Flagstaff, AZ (US); Brandon A. Lurie, Flagstaff, AZ (US); Craig R. McMurray, Flagstaff, AZ (US); William D. Montgomery, Flagstaff, AZ (US); Wendy J. Terry, Anthem, AZ (US); Eric M. Tittelbaugh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/820,615

(22) Filed: Nov. 22, 2017

(65) Prior Publication Data
US 2018/0153718 A1 Jun. 7, 2018

Related U.S. Application Data

(63) Continuation of application No. 13/298,060, filed on Nov. 16, 2011, now Pat. No. 9,839,540.
(Continued)

(51) Int. Cl.
*A61F 2/915* (2013.01)
*A61F 2/88* (2006.01)
(Continued)

(52) U.S. Cl.
CPC ............... *A61F 2/88* (2013.01); *A61F 2/07* (2013.01); *A61F 2/915* (2013.01); *A61F 2/966* (2013.01);
(Continued)

(58) Field of Classification Search
CPC .. A61F 2/88; A61F 2/915; A61F 2002/91508; A61F 2002/91516; A61F 2002/91525
See application file for complete search history.

(56) References Cited

U.S. PATENT DOCUMENTS 3,953,566 A 4/1976 Gore
4,187,390 A 2/1980 Gore
(Continued)

FOREIGN PATENT DOCUMENTS

CN 101926699 A 12/2010
EP 0293090 A2 11/1988
(Continued)

OTHER PUBLICATIONS

Extended European Search Report issued in EP Application No. 17186750.0, dated Oct. 24, 2017, 7 pages.
(Continued)

*Primary Examiner* — Suba Ganesan

(57) ABSTRACT

The invention relates to a medical device and a method of using it. The device is a stent which can be percutaneously deliverable with (or on) an endovascular catheter or via other surgical or other techniques and then expanded. The stent is configured to have a central portion defined by "open" cells and at least two end portions, defined by "closed" cells, spaced apart and directly connected to the distal and proximal ends of the central portion of the stent. The stent may also optionally have a covering or a lattice with openings.

20 Claims, 19 Drawing Sheets

Related U.S. Application Data

(60) Provisional application No. 61/523,115, filed on Aug. 12, 2011, provisional application No. 61/433,069, filed on Jan. 14, 2011.

(51) Int. Cl.
  *A61F 2/07* (2013.01)
  *A61F 2/966* (2013.01)
  *A61F 2/958* (2013.01)

(52) U.S. Cl.
  CPC ............ *A61F 2002/075* (2013.01); *A61F 2002/91558* (2013.01); *A61F 2002/91575* (2013.01); *A61F 2002/9583* (2013.01); *A61F 2220/005* (2013.01); *A61F 2220/0075* (2013.01); *A61F 2230/0054* (2013.01)

(56) References Cited

U.S. PATENT DOCUMENTS

| | | | |
|---|---|---|---|
| 4,877,661 A | 10/1989 | House et al. |
| 4,955,899 A | 9/1990 | Della Corna et al. |
| 5,026,513 A | 6/1991 | House et al. |
| 5,071,609 A | 12/1991 | Tu et al. |
| 5,476,589 A | 12/1995 | Bacino |
| 5,534,007 A | 7/1996 | St. Germain et al. |
| 5,549,663 A | 8/1996 | Cottone et al. |
| 5,708,044 A | 1/1998 | Branca |
| 5,718,973 A | 2/1998 | Lewis et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Gore et al. |
| 5,853,419 A | 12/1998 | Imran |
| 5,925,061 A | 7/1999 | Ogi et al. |
| 5,935,162 A | 8/1999 | Dang |
| 6,010,529 A | 1/2000 | Herweck et al. |
| 6,013,854 A | 1/2000 | Moriuchi |
| 6,042,588 A | 3/2000 | Munsinger et al. |
| 6,042,605 A | 3/2000 | Martin et al. |
| 6,042,606 A | 3/2000 | Frantzen |
| 6,174,329 B1 | 1/2001 | Callol et al. |
| 6,190,406 B1 | 2/2001 | Duerig et al. |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,336,937 B1 | 1/2002 | Vonesh et al. |
| 6,352,552 B1* | 3/2002 | Levinson ............... A61F 2/91 623/1.15 |
| 6,436,132 B1 | 8/2002 | Patel et al. |
| 6,488,701 B1 | 12/2002 | Nolting et al. |
| 6,541,589 B1 | 4/2003 | Baillie |
| 6,620,190 B1 | 9/2003 | Colone |
| 6,626,939 B1 | 9/2003 | Burnside et al. |
| 6,673,102 B1 | 1/2004 | Vonesh et al. |
| 6,673,107 B1 | 1/2004 | Brandt et al. |
| 6,730,120 B2 | 5/2004 | Berg et al. |
| 6,755,856 B2 | 6/2004 | Fierens et al. |
| 6,758,858 B2 | 7/2004 | McCrea et al. |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,306,729 B2 | 12/2007 | Bacino et al. |
| 7,419,678 B2 | 9/2008 | Falotico |
| 7,531,611 B2 | 5/2009 | Sabol et al. |
| 7,789,908 B2 | 9/2010 | Sowinski et al. |
| 7,811,314 B2 | 10/2010 | Fierens et al. |
| 7,815,763 B2 | 10/2010 | Fierens et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 8,585,753 B2 | 11/2013 | Scanlon et al. |
| 9,345,601 B2 | 5/2016 | Jantzen et al. |
| 9,795,496 B2 | 10/2017 | Armstrong et al. |
| 9,931,193 B2 | 4/2018 | Cully et al. |
| 2001/0053929 A1 | 12/2001 | Vonesh et al. |
| 2002/0198588 A1 | 12/2002 | Armstrong et al. |
| 2003/0055494 A1 | 3/2003 | Bezuidenhout et al. |
| 2003/0060871 A1 | 3/2003 | Hill et al. |
| 2003/0180488 A1 | 9/2003 | Lim et al. |
| 2004/0024442 A1 | 2/2004 | Sowinski et al. |
| 2004/0024448 A1 | 2/2004 | Chang et al. |
| 2004/0044400 A1 | 3/2004 | Cheng et al. |
| 2004/0044401 A1 | 3/2004 | Bales et al. |
| 2004/0133266 A1 | 7/2004 | Clerc et al. |
| 2004/0170782 A1 | 9/2004 | Wang et al. |
| 2004/0224442 A1 | 11/2004 | Grigg |
| 2004/0260277 A1 | 12/2004 | Maguire |
| 2005/0080476 A1 | 4/2005 | Gunderson et al. |
| 2005/0137680 A1 | 6/2005 | Ortiz et al. |
| 2005/0283224 A1 | 12/2005 | King |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0106337 A1 | 5/2006 | Blankenship |
| 2006/0118236 A1 | 6/2006 | House et al. |
| 2006/0135985 A1 | 6/2006 | Cox et al. |
| 2006/0161241 A1 | 7/2006 | Barbut et al. |
| 2006/0190070 A1 | 8/2006 | Dieck et al. |
| 2006/0259133 A1 | 11/2006 | Sowinski et al. |
| 2006/0271091 A1 | 11/2006 | Campbell et al. |
| 2006/0276883 A1 | 12/2006 | Greenberg et al. |
| 2007/0012624 A1 | 1/2007 | Bacino et al. |
| 2007/0060999 A1 | 3/2007 | Randall et al. |
| 2007/0129786 A1 | 6/2007 | Beach et al. |
| 2007/0207186 A1 | 9/2007 | Scanlon et al. |
| 2007/0207816 A1 | 9/2007 | Spain |
| 2007/0208421 A1 | 9/2007 | Quigley |
| 2007/0213800 A1 | 9/2007 | Fierens et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0051876 A1 | 2/2008 | Ta et al. |
| 2008/0097301 A1 | 4/2008 | Alpini et al. |
| 2008/0097579 A1* | 4/2008 | Shanley ............... A61F 2/88 623/1.16 |
| 2008/0097582 A1 | 4/2008 | Shanley et al. |
| 2008/0119943 A1 | 5/2008 | Armstrong et al. |
| 2008/0319531 A1 | 12/2008 | Doran et al. |
| 2009/0005854 A1 | 1/2009 | Huang et al. |
| 2009/0030499 A1 | 1/2009 | Bebb et al. |
| 2009/0043373 A1 | 2/2009 | Arnault De La Menardiere et al. |
| 2009/0182413 A1 | 7/2009 | Burkart et al. |
| 2009/0306766 A1 | 12/2009 | McDermott et al. |
| 2010/0016940 A1 | 1/2010 | Shokoohi et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0159171 A1 | 6/2010 | Clough |
| 2010/0256738 A1 | 10/2010 | Berglund |
| 2010/0286760 A1 | 11/2010 | Beach et al. |
| 2011/0087318 A1 | 4/2011 | Daugherty et al. |
| 2012/0323211 A1 | 12/2012 | Ogle et al. |
| 2013/0131780 A1 | 5/2013 | Armstrong et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0253466 A1 | 9/2013 | Campbell et al. |
| 2013/0297003 A1 | 11/2013 | Pinchuk |
| 2014/0135897 A1 | 5/2014 | Cully et al. |
| 2014/0172066 A1 | 6/2014 | Goepfrich et al. |
| 2014/0180402 A1 | 6/2014 | Bruchman et al. |
| 2015/0313871 A1 | 11/2015 | Li et al. |

(56) References Cited

U.S. PATENT DOCUMENTS

| | | |
|---|---|---|
| 2016/0015422 A1 | 1/2016 | De Cicco et al. |
| 2017/0065400 A1 | 3/2017 | Armstrong et al. |

FOREIGN PATENT DOCUMENTS

| | | | |
|---|---|---|---|
| EP | 0313263 | A2 | 4/1989 |
| EP | 0775472 | A2 | 5/1997 |
| EP | 0815806 | A2 | 1/1998 |
| EP | 0893108 | A2 | 1/1999 |
| EP | 2255750 | A2 | 12/2010 |
| JP | H09241412 | A | 9/1997 |
| JP | H11290448 | A | 10/1999 |
| JP | 2001509702 | A | 7/2001 |
| JP | 2010504174 | A | 2/2010 |
| JP | 2010535075 | A1 | 11/2010 |
| WO | WO9416802 | A1 | 8/1994 |
| WO | WO9505555 | A1 | 2/1995 |
| WO | WO9607370 | A1 | 3/1996 |
| WO | 1996040348 | A1 | 12/1996 |
| WO | WO9710871 | A1 | 3/1997 |
| WO | 1999026558 | A1 | 6/1999 |
| WO | WO0041649 | A1 | 7/2000 |
| WO | WO0047271 | A1 | 8/2000 |
| WO | WO0174272A2 | A2 | 10/2001 |
| WO | WO02060506 | A1 | 8/2002 |
| WO | 2003003946 | A1 | 1/2003 |
| WO | 2004000375 | A1 | 12/2003 |
| WO | 2006019626 | A2 | 2/2006 |
| WO | 2006058322 | A2 | 6/2006 |
| WO | 2008021002 | A1 | 2/2008 |
| WO | 2008028964 | A2 | 3/2008 |
| WO | 2008036870 | A2 | 3/2008 |
| WO | 2008049045 | A2 | 4/2008 |
| WO | 2009017827 | A1 | 2/2009 |
| WO | 2009100210 | A1 | 8/2009 |
| WO | 2009108355 | A1 | 9/2009 |
| WO | 2010006783 | A1 | 1/2010 |
| WO | 2010008570 | A1 | 1/2010 |
| WO | 2010030766 | A1 | 3/2010 |
| WO | 2010132707 | A1 | 11/2010 |
| WO | 2010150208 | A2 | 12/2010 |
| WO | 2011098565 | A1 | 8/2011 |
| WO | 2013109337 | A1 | 7/2013 |

OTHER PUBLICATIONS

International Search Report and Written Opinion for PCT/US2014/068430 dated Feb. 20, 2015, corresponding to U.S. Appl. No. 14/558,296, 9 pages.
International Search Report and Written Opinion issued in PCT/US2011/061165, dated Oct. 1, 2012, 20 pages.
International Search Report and Written Opinion issued in PCT/US2012/064908, dated Feb. 4, 2013, 10 pages.
International Search Report and Written Opinion issued in PCT/US2012/066518, dated Feb. 4, 2013, 10 pages.
International Search Report and Written Opinion issued in PCT/US2012065066, dated Nov. 11, 2013, 9 pages.
International Search Report and Written Opinion issued in PCT/US2016/028671, dated Jul. 28, 2016, 19 pages.
International Search Report issued in PCT/US2013/076405, dated May 6, 2014, 7 pages.
International Search Report issued in PCT/US2014/013496, dated Dec. 2, 2014, 3 pages.
Nakayama, Yasuhide. Microporous Stent Achieves Brain Aneurysm Occlusion Without Disturbing Branching Flow. NeuroNews Nov. 2012; 8:1-2.
Nishi S, Nakayama Y, lshibashi-Ueda H, Okamoto Y, Yoshida M. Development of microporous self-expanding stent grafts for treating cerebral aneurysms: designing micropores to control intimal hyperplasia. J Artif Organs 2011; 14:348-356.
International Preliminary Report on Patentability issued in PCT/US2016/028671, dated Nov. 2018, 12 pages.

\* cited by examiner

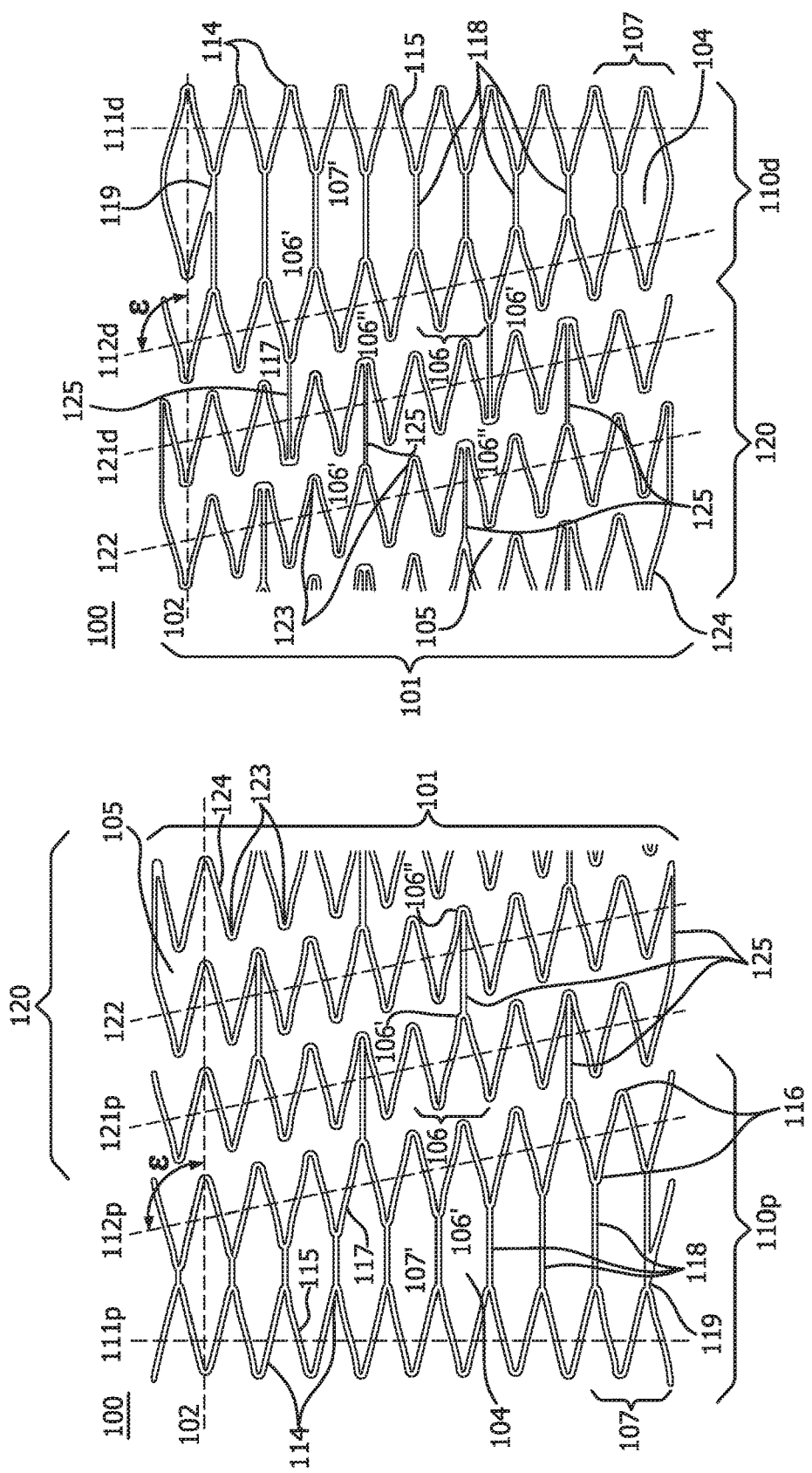

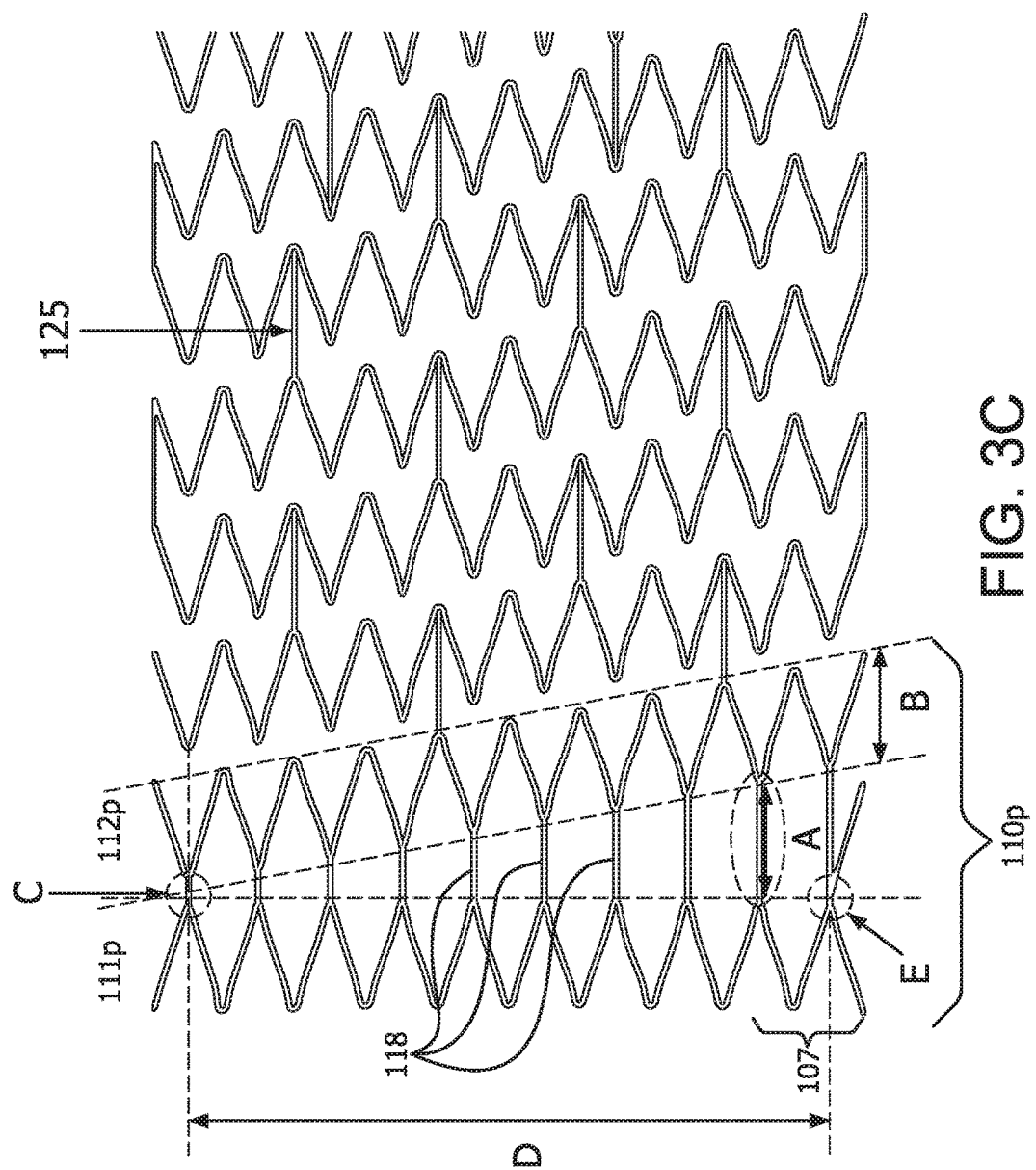

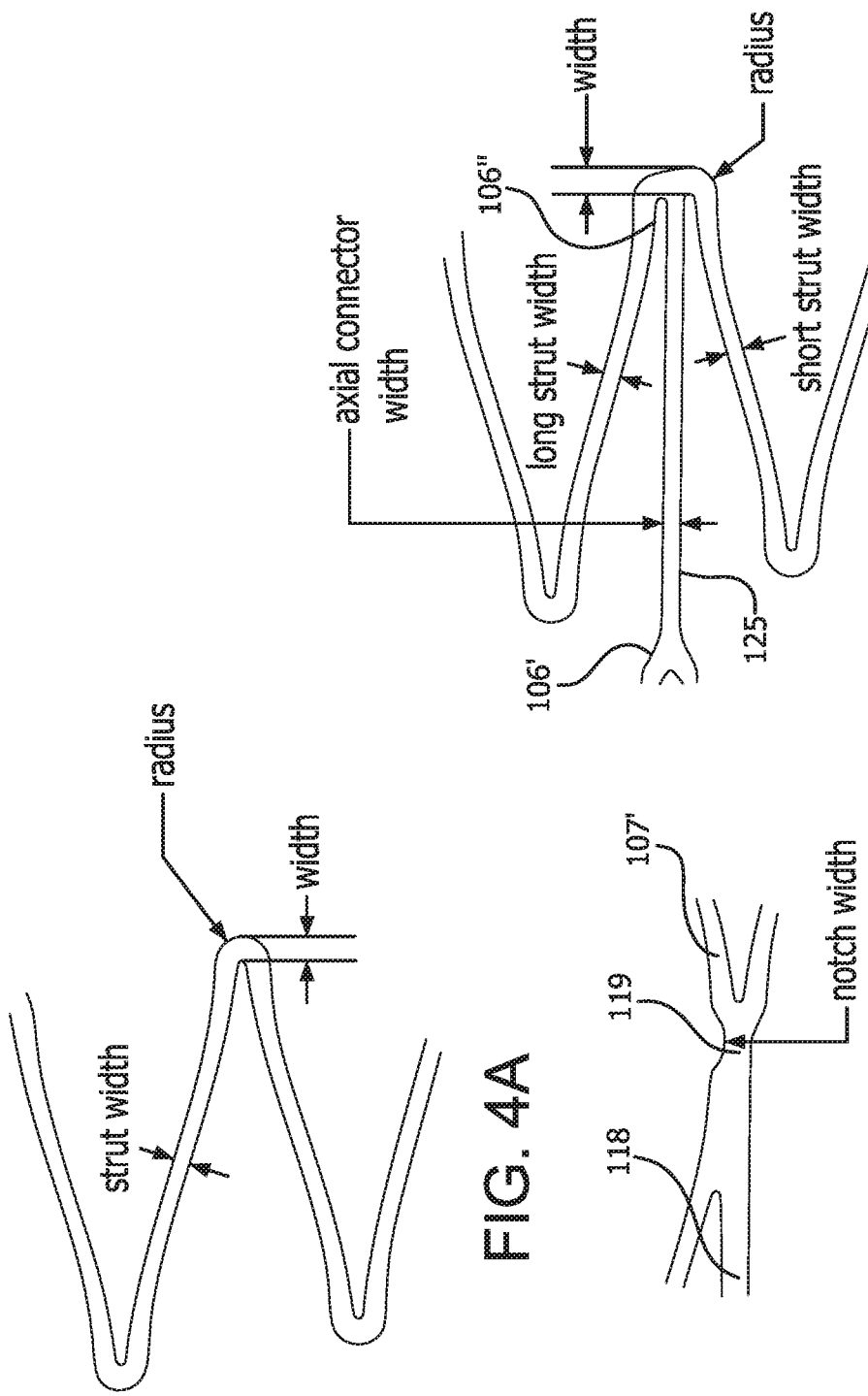

STENT

CROSS-REFERENCE TO A RELATED APPLICATION

This application is a continuation of U.S. application Ser. No. 13/298,060, filed Nov. 16, 2011, which claims the priority benefit under 35 U.S.C. § 119(e) of U.S. Provisional Application No. 61/433,069 filed on Jan. 14, 2011 and U.S. Provisional Application No. 61/523,115 filed on Aug. 12, 2011, the contents of which are incorporated herein in their entireties.

FIELD OF THE INVENTION

The invention relates generally to medical implants for supporting, maintaining, or repairing a lumen, passageway or opening in a living body and to methods of using them. In particular, the invention relates to medical devices that are designed to be inserted endoluminally into a body.

BACKGROUND OF THE INVENTION

Medical stents are generally known. One use for medical stents is to expand a body lumen, such as a blood vessel, which has contracted in diameter through, for example, the effects of lesions called atheroma or the occurrence of cancerous tumors. Atheroma refers to lesions within arteries that include plaque accumulations that can obstruct blood flow through the vessel. Over time, the plaque can increase in size and thickness and can eventually lead to clinically significant narrowing of the artery, or even complete occlusion. When expanded against the body lumen, which has contracted in diameter, the medical stents provide a tube-like support structure inside the body lumen. Stents, in combination with coverings, also can be used for the endovascular repair of aneurysms, an abnormal widening or ballooning of a portion of a body lumen which can be related to weakness in the wall of the body lumen. Various stent designs are known in the art. Stents typically are tubular, and are expandable or self-expand from a relatively small diameter to a larger diameter.

SUMMARY OF THE INVENTION

Devices according to this application are suitable for implantation into various body vessels or openings, such as the carotid artery.

One exemplary device is a stent having a body with distal and proximal ends and defines a central lumen along a longitudinal axis. The body has an insertion configuration with a reduced profile, and a deployed configuration with an enlarged profile greater than the insertion profile. The body includes spaced apart, undulating circumferential members, as well as an undulating helical element. The helical element extends helically about the longitudinal axis, and is axially interposed between and directly connected to the circumferential members. The helical element defines open cells, while the circumferential members define closed cells.

Another exemplary device is a stent having distal and proximal ends, and defining a central lumen along a longitudinal axis. The stent has an insertion configuration with a reduced profile and a deployed configuration with an enlarged profile greater than the reduced profile. The stent has several portions. To define a closed cell structure, the stent has a plurality of spaced apart, undulating circumferential members with one undulating helical turn and one or more undulating circumferential rings. To define an open cell structure, the stent also has a helical element extending along the longitudinal axis axially interposed between the undulating circumferential members with a plurality of helical turns. The undulating helical turn of the circumferential member is directly connected to the helical body. Together, the undulating helical turn and the helical body defined a uniform apex geometry.

Another exemplary device is a stent having distal and proximal ends and defining a central lumen along a longitudinal axis. The stent has an insertion configuration with a reduced profile and a deployed configuration with an enlarged profile greater than the reduced profile. The stent has a plurality of spaced apart, undulating circumferential members having one undulating helical turn and one or more undulating circumferential rings that define a closed cell structure, and a helical element extending along the longitudinal axis axially and interposed between the undulating circumferential members. The helical element has one helical turn or less than one helical turn, such as a portion of a helical turn, that define an open cell structure. The undulating helical turn of the circumferential member is directly connected to the helical body. Together, the undulating helical turn and the helical body defined a uniform apex geometry.

Yet another exemplary device is an endovascular prosthesis with a stent. The prosthesis has a lattice, which defines a plurality of openings. The lattice has at least two continuous longitudinal segments, and at least two continuous circumferential segments. The longitudinal segments are substantially parallel to a longitudinal axis of the prosthesis. The circumferential segments are oriented at an angle of between about 45° and about 90° with respect to the longitudinal axis.

Yet still another exemplary device is an endovascular prosthesis having a lumen defining a longitudinal axis. The prosthesis has a stent having a framework of struts including a plurality of longitudinal connectors. The prosthesis also has a polymeric lattice that defines a plurality of openings. The lattice has a plurality of continuous longitudinal segments that extend in a direction that is substantially parallel to the longitudinal axis of the stent. In addition, the lattice also has a plurality of continuous circumferential segments at an angle with respect to the longitudinal axis of the stent. At least a portion of the longitudinal segments is aligned with and affixed to the longitudinal connectors of the stent.

The devices described herein have various uses. An exemplary use is in a method of treating stenosis in a carotid artery. For example, the device is a stent with an insertion configuration with a reduced profile and a deployed configuration with an enlarged profile greater than the insertion profile. The stent also has a plurality of spaced apart, undulating circumferential members, and an undulating helical element extending helically about the longitudinal axis. The undulating helical element is axially interposed between and directly connected to the circumferential members. The undulating helical element defines a plurality of open cells. The circumferential member defines a plurality of closed cells. This stent is inserted into the vasculature of the patient. The stent is then positioned and deployed within the carotid artery.

Numerous variations and modifications of these exemplary stents, prostheses and methods of using them are contemplated. Additional features and advantages of the invention will be set forth in the description or can be learned by practice of the invention. These features and other advantages of the invention will be realized and attained by the structure particularly pointed out in the written description and claims hereof as well as the appended drawings.

It is to be understood that both the foregoing general description and the following detailed description are exemplary and explanatory, and are intended to provide further explanation of the invention as claimed.

BRIEF DESCRIPTION OF THE DRAWINGS

The accompanying drawings are included to provide a further understanding of the invention, and are incorporated in and constitute a part of this specification, illustrate embodiments of the invention, and together with the description serve to explain the principles of the invention.

In the drawings:

FIG. 3A is a partial plan view of a stent (full circumference shown) showing an apex geometry between the apices in the helical turn and the circumferential ring of the circumferential member and the interrelationship between the open- and closed-cell configuration at one end.

FIG. 3B is a partial plan view of a stent (full circumference shown) showing an apex geometry between the apices in the helical turn and the circumferential ring of the circumferential member and an interrelationship between the open- and closed-cell lattices at the opposite end as that shown in FIG. 3A;

FIG. 3C is plan view of a stent (full circumference shown), which illustrates a relationship between a circumferential ring and a helical turn of the circumferential member of a stent;

FIG. 4A is a partial plan view of a stent, which illustrates geometry of undulating helical turns without axial connectors between adjacent undulations;

FIG. 4B is a partial plan view of a stent, which illustrates geometry of undulating helical turns with axial connectors between adjacent undulations;

FIG. 4C is a partial plan view of a notch connection made between the last strut of the last apex in the helical turn of the circumferential member and the apex of the adjacent circumferential ring;

DETAILED DESCRIPTION OF THE ILLUSTRATED EMBODIMENTS

Figure 1:
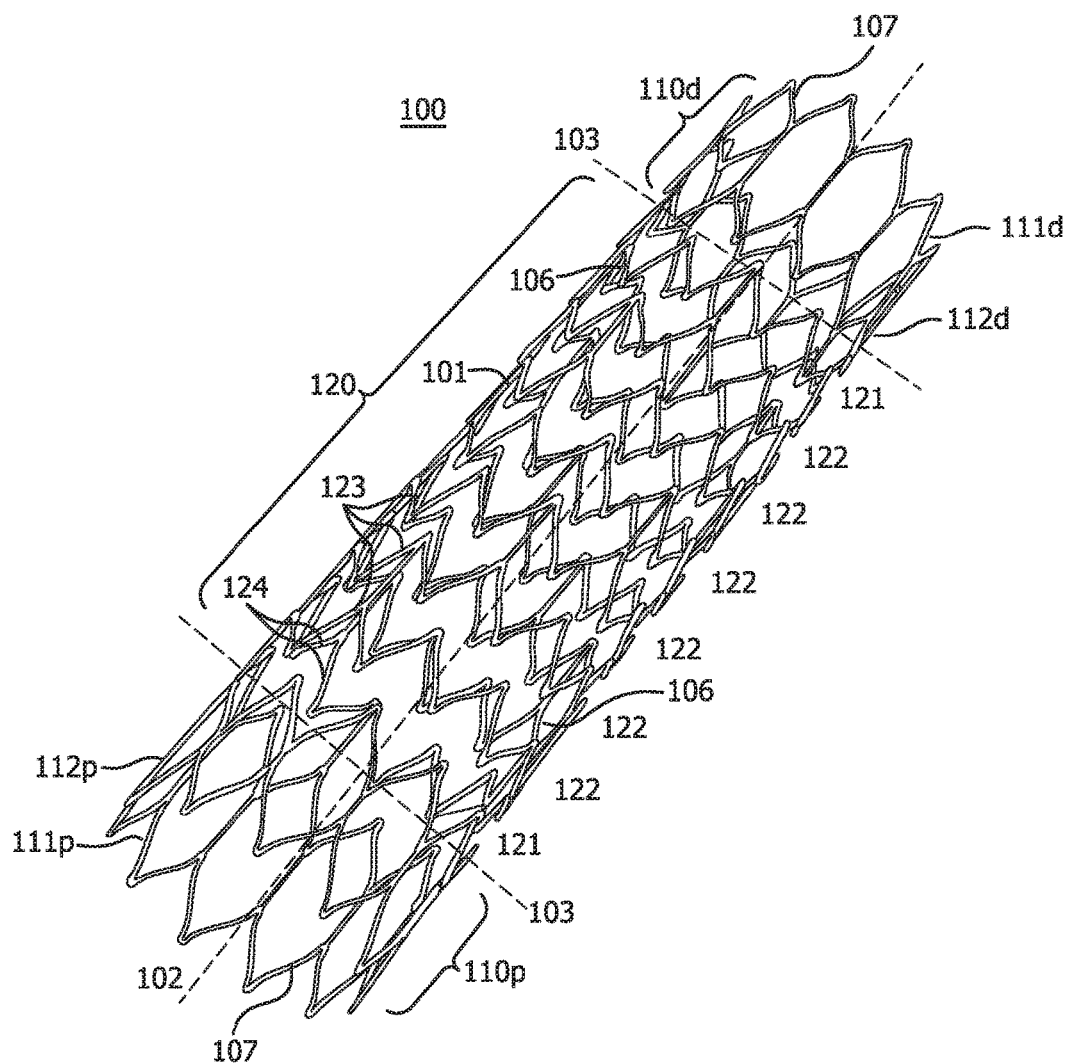
FIG. 1 is a perspective view of a stent with eleven distal and eleven proximal facing apices per circumferential turn.

A stent is a device adapted to be inserted into a body and then deployed within the body, such as the carotid artery. A stent has a framework of struts or relatively rigid sections. Most generally, stents assist in structurally supporting the host vessel lumen, maintaining patency through the vessel, passageway or opening, repairing vessels having an intimal flap or dissection, or isolating sections of a host vessel lumen, such as aneurysms.

Stents can be formed from either an elastic or springy material that will self-expand in place following placement or a plastically deformable material that is expanded in place using a balloon or similar device. For example, a sheath can compress the stent so that it can be inserted into a patient, and removal of the compressive force applied by the sheath (such as by retracting the sheath) allows the stent to self-expend for deployment. Likewise, the stents can also be configured to have a covering, to be a permanent implant, or to erode/resorb over time, and/or to have a substrate for elution of drugs.

In most general terms, the stent has an insertion configuration with a reduced profile that permits intraluminal or endoluminal delivery of the stent into a vessel lumen, and a deployed configuration with an enlarged profile greater than the insertion profile that provides structural support for the vessel. For example, a stent has a tubular body capable of self-expanding from a reduced diameter insertion configuration to an enlarged diameter deployed configuration at, for example, a temperature of about 10° C., about 20° C., or about 34° C. The reduced and enlarged profiles can include various shapes, including circular profiles and non-circular profiles (such as ovals, for example).

The length of the stent remains relatively constant as the stent transforms from the insertion configuration to the deployed configuration; it does not substantially foreshorten. The overall length of the stent in the deployed configuration is within, for example, ±10%, ±5%, ±4%, or ±2% of the length of the stent in the insertion configuration. It is possible, however, to design a stent in accordance with this disclosure that does foreshorten by more than 10% if that is deemed desirable.

When the stent is cylindrical, the reduced and enlarged profiles can be generally circular. In that instance, the stent body has a first diameter (d1) in the deployed configuration, and a second diameter (d2) in the insertion configuration. A ratio of the first diameter to the second diameter (d1:d2) can be greater than about 2:1, between 3.6:1 and 10:1, or between 4:1 and 7:1.

The illustrated stents have circumferential members and helical elements that have undulations. The undulations are formed by struts interconnected at bends or apices of the stent body, and arranged into wave-like configurations. The undulations can form various patterns, such as sinusoidal patterns, zigzag patterns or similar geometric patterns. The undulations of the helical element can form a series of rows or turns along the length of the stent body.

In addition, connectors extend between portions of the circumferential members and portions of the helical elements, or between various portions of the helical elements. Peaks are formed where a connector extends outwardly from an apex. Valleys are formed where a connector extends into an apex.

Most generally, the stents described herein have a closed cell portion and an open cell portion. Connections between longitudinally adjacent portions of the stent body define the open and closed cells. In the portion of the stent with open cells, there are intermittent regular connections (for example, connectors are provided at every second apex) or intermittent irregular connections (for example, connectors are provided at the first, third, seventh, tenth apex). That is, at least some apices are not connected to longitudinally adjacent rows. In the portion of the stent with closed cells, there are regular connections between longitudinally adjacent rows. Each of the apices in a closed cell structure is connected to a longitudinally adjacent turn.

Due to its open cell portion with only intermittent connections between the undulations of each adjacent row, the stent can have a relatively high degree of longitudinal flexibility before expansion. Such flexibility can permit advancement through torturous pathways of relatively small diameter. The open cell portion of the stent also can have a high degree of longitudinal flexibility after expansion. Such flexibility can provide a high degree of conformance with various vessel shapes. Finally, the stent can have enhanced crush-resistance and fatigue performance to maintain patency of the lumen into which it is implanted.

In its simplest form, the stent can have a single circumferential member (CM) that defines closed cell structures, and a single helical element (HE) that defines open cell structure as follows:

CM-HE

Other stents can have three portions. Circumferential members can be provided at the ends. Between these circumferential members is a generally helical element with a series of helical turns, as follows:

CM-HE-CM

Alternatively, the stent can have more than three portions. For example, three circumferential members can be provided at the distal and proximal ends and also between those ends. These circumferential members are interconnected via two generally helical elements with a series of helical turns:

CM-HE-CM-HE-CM

In each of these stents, the circumferential members and the helical elements are directly connected. A continuous pattern of undulations joins the circumferential member to the helical elements. For example, where the circumferential member has an undulating circumferential ring and a helical turn attached to the ring, a continuous helical pattern is formed about the longitudinal axis between the helical element and the helical turns of the circumferential members. There are no intermediate or transition stages between the helical element and the circumferential members.

Multiple stents can be joined together various ways to form, for example, a bifurcated stent device, or stent device with a side branch, or other complex structure. The stents can be joined together by one or more sutures, or polymeric or metallic hinges. The stents can be joined together by flexible polymeric connecting elements (polymeric webs) that connect adjacent, spaced-apart stent elements (shown as ≡). For example, a prosthesis having the following stent structure can be formed by adhering a covering (described below) to join the end circumferential members to the central stent:

CM≡CM-HE-CM≡CM

Another option is to weld the multiple stents together. A further option is to assemble the stents endovascularly in an overlapping fashion.

Various coverings can be provided on the interior or exterior surfaces of the stent or both. Such covered stents can be used to isolate cells, aneurysms, vessel wall defects, and the like. Suitable cover materials include bioabsorbable polymer (such as polylactic acid, poly(trimethylene carbonate) or PGA/TMC), fluoropolymer (such as fluorinated ethylene propylene or FEP, polytetrafluoroethylene or PTFE and expanded fluoropolymer, such as expanded polytetrafluoroethylene or ePTFE), fluoroelastomer (for example, TFE/PMVE copolymers), polyester (such as polyethylene terephthalate or PET), polyethylene, polypropylene, polyurethane, metal mesh (such as a woven or cut nitinol sheet) silicone, etc.

Optionally, the cover material can form a lattice having a plurality of openings. Such a lattice covering can have various uses. For example, a lattice covered stent can provide plaque stabilization and scaffolding, while simultaneously allowing perfusion of blood from the inner lumen of the stent if the openings are sized appropriately. This can be beneficial, for example, to perfuse side branch blood vessels. Alternatively, the relatively small lattice openings can be provided (for example about 40 or 50 µm) to relieve pressure from weakened portions of a blood vessel (for example, to treat a cerebral aneurysm). The relatively small lattice openings also can be useful for preventing encroachment of tissue from the patient into the inner lumen of the stent (for example, when the stent is placed near cancerous tissue), while still permitting side branch perfusion.

FIG. 1 depicts a self-expanding stent 100 with a cylindrical body 101. The stent can be made in various forms including various lengths and inside diameters. It can also be tapered along all or a portion of its length so that the inside diameter changes along the length. A tapered length section may be located closer to either end of the graft, or the taper may exist as a uniform, gradual taper extending between the graft ends.

A continuous pattern of undulations 106 forms a series of helical turns about the longitudinal axis 102. Those helical turns 121, 122 can form a substantially cylindrical, tubular helical element 120. Alternatively, the helical turns 121, 122 can form a tapered, tubular helical element.

The helical turns 121, 122 have a number of apices 123. These apices 123 are formed where two or more struts 124 interconnect. The stent illustrated in FIG. 1 can be called an eleven-apex stent, because it has eleven apices per circumferential row facing in a single direction (either facing distally or proximally).

In FIG. 1, the helical element 120 is axially interposed between and directly connected to the circumferential members 110 (p—proximal and d—distal). Each of the circumferential members 110p or 110d has one undulating helical turn 112p or 112d with a pattern of undulations 106 connected to an undulating circumferential ring 111p or 111d with a pattern of undulations 107. The circumferential member 110p or 110d and the helical body 120 meet at division 103.

Figure 2A:
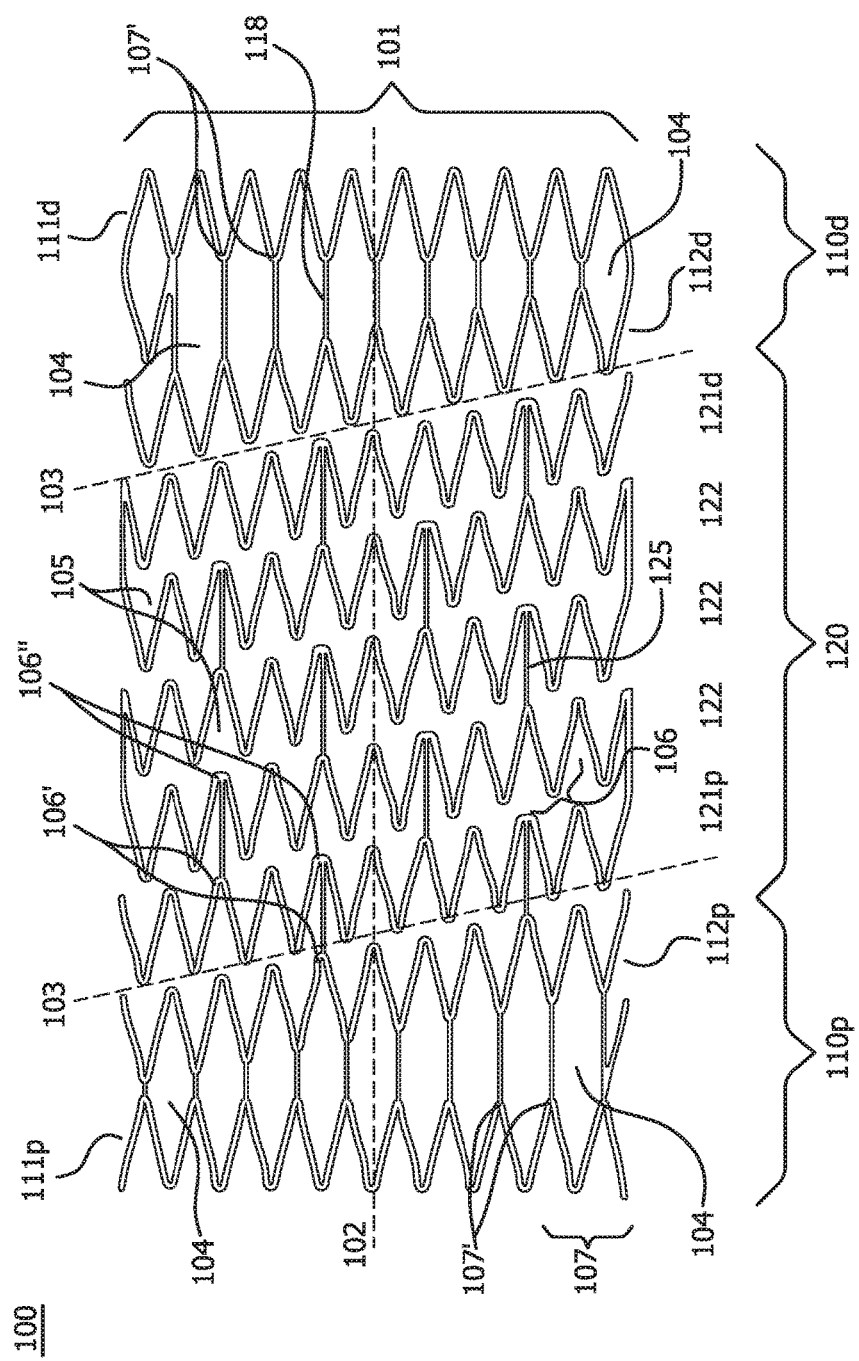
FIGS. 2A and 2B are plan views of a stent (full circumference shown), which illustrates an interrelationship between the circumferential members and the helical element (5 helical turns—FIG. 2A, and 8 helical turns—FIG. 2B)
Figure 2B:
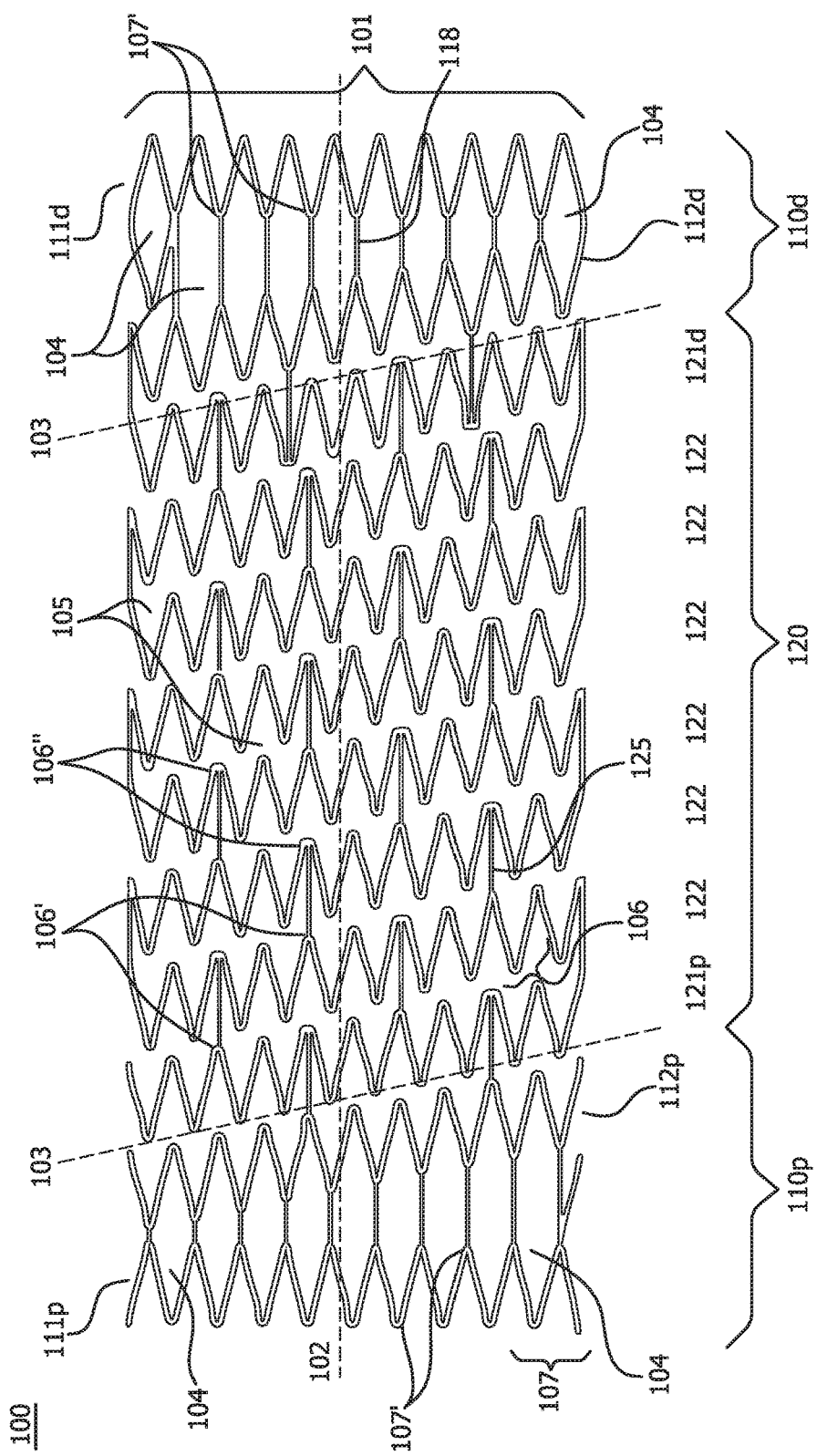

Within the stent, various connecting struts can be provided to contribute to longitudinal stability to the stent. For example, these connecting struts or connectors can join adjacent structures, turns or rows of the stent. In FIGS. 2A and 2B, the undulations 106 and 107 in the stent body 101 form peaks 106' or 107' where a connector 118, 125 extends outwardly from an apex, and form valleys 106" where a connector 125 extends into an apex.

In FIGS. 3A and 3B, closed cell connectors 118 join the helical turn 112p or 112d and the circumferential ring 111p or 111d formed by undulations 107 on the circumferential member 110p or 110d. Axial connectors 125 join adjacent undulations 106 of the helical element 120, and also join the helical turn 112p or 112d of the circumferential member 110p or 110d and undulations 106 of the helical element 120 (connections between 112p-121p, 121p-122 . . . 122-121d, and 121d-112d).

In FIG. 3C, the lengths of closed cell connectors 118 vary. As depicted, the lengths of the closed cell connectors 118 can increase uniformly along a circumferential direction of the stent from the closed cell connector 118 at region C, which can have lengths of about 0.3 mm to about 3.0 mm, and a width about the same as the width of the axial connector 125 (see Table 1). On the other hand, the closed cell connector 118 at region A can have the same or substantially the same length as the amplitude B of each undulation 107 in the helical turn 112p of the circumferential member 110p. Region E defines a notch 119 as shown in FIG. 3A. If it deemed desirable, the lengths of the closed cell connectors 118 can adjusted so that one or more of the circumferential rings 111p (or 111d as shown in FIG. 3B) at the end of the stent define a plane orthogonal to the longitudinal axis.

The closed cell connectors 118 and axial connectors 125 of FIGS. 3A and 3B, are depicted extending substantially parallel to the longitudinal axis 102 of the stent body 101. However, the closed cell connectors 118, axial connectors 125, or both need not be parallel to the longitudinal axis and can extend in a direction to the longitudinal axis at any angle (such as between about −90° and about 90° from the longitudinal axis), or may not even be substantially straight. For example, the closed cell connectors 118 can extend substantially parallel to the longitudinal axis 102, while the axial connectors 125 form an angle to the longitudinal axis 102 of the stent body 101. Alternatively, the axial connectors 125 can extend substantially parallel to the longitudinal axis 102, while the closed cell connectors 118 form an angle to the longitudinal axis 102 of the stent body 101. Further still, the closed cell connectors 118 can be bent, for example roughly in the shape of the letter V or can include one or more curved portions.

The circumferential members 110p and 110d have closed cells 104 in the stent shown in FIGS. 3A and 3B. The closed cells can have six sides or less. A side may be straight or have curvature. As depicted, some of the closed cells have a substantially hexagonal shape, and others have a substantially rhombic shape. Other shapes or combinations of shapes are possible such as various regular or irregular shapes.

In FIGS. 3A and 3B, an undulating circumferential ring 111p or 111d of the circumferential member 110p or 110d has a series of apices 114 in each undulation 107. An undulating helical turn 112p or 112d of the circumferential member 110p or 110d also has a series of apices 116 in each undulation 106. Closed cell connectors 118 extend between peaks 106' of the undulating helical turn 112p or 112d and peaks 107' of the adjacent undulating circumferential ring 111p or 111d at the proximal and distal ends of the stent 100, respectively. Alternatively, the closed cell connectors 118 within the undulating circumferential members 110p and 110d can extend from a valley to a valley, from a peak to a valley, or from a valley to a peak.

The stent of FIGS. 3A and 3B also has open cells 105. The open cells 105 can have seven sides or more. Axial connectors 125 extend intermittently between longitudinally adjacent turns of the undulating helical element 120. These axial connectors 125 join pairs undulations 106 on the adjacent turns [112p-121p, 121p-122 . . . 122-121d, and 121d-112d]. The shape of the open cells depicted in these figures is exemplary. Likewise, the open cells shown in FIGS. 3A and 3B are defined by regular, intermittent axial connectors 125. Alternatively, the open cells can be formed by irregular, intermittent axial connectors.

FIGS. 3A and 3B further illustrate direct connections between the helical element 120 and the circumferential members 110p and 110d. The undulating helical element 120 has a series of helical turns [121p, 121d, 122, etc.] about the longitudinal axis 102. The circumferential member 110p or 110d also has an undulating helical turn 112p or 112d. The undulations 106 of the helical turn 121p or 121d of the undulating helical element 120 form continuous helical pattern with the undulations 106 of the undulating helical turn 112p or 112d of the circumferential member 110p or 110d without any intermediate or transition stages in-between. Such continuous helical pattern defines a direct connection between the helical element 120 and the circumferential members 110p and 110d.

FIGS. 3A and 3B also illustrate apex geometry. Apex geometry refers to configuration of the apices 114, 116, 123 where two or more struts 115, 117, 124 meet, respectively. Each strut and each apex has a cross-section with a width, and a thickness (into the page). Apex radius, width, and thickness (see FIGS. 4A-4C), and the angles of the struts forming those apices substantially define the apex geometry. The undulating helical turn 112p or 112d of the circumferential member 110p or 110d and the helical turns 121p, 121d, 122 of the helical element 120 have a substantially uniform apex geometry. Optionally, the circumferential ring 111p or 111d also has the same apex geometry as the undulating helical turn 112p or 112d of the circumferential member 110p or 110d and the helical turns 121p, 121d, 122 of the helical element 120. It is also possible for the apex geometry to be varied. For example, the circumferential ring 111p or 111d, undulating helical turn 112p or 112d of the circumferential member 110p or 110d and the helical turns 121p, 121d, 122 of the helical element 120 can each have different apex geometries.

The circumferential members 110p and 110d have at least two undulating structures. The circumferential members 110p and 110d are depicted with one undulating helical turn 112p or 112d and an undulating circumferential ring 111p or 111d.

The circumferential member 110p or 110d of FIG. 2A has the same number apices in the undulating helical turn 112p or 112d and the circumferential ring 111p or 111d. The amplitudes of the undulating helical turn 112p or 112d and the circumferential ring 111p or 111d are substantially the same. It is possible, however, that the circumferential ring 111p or 111d can have a greater or lesser number of apices than the helical turn 112p or 112d. The circumferential ring 111p or 111d can have a greater or lesser amplitude than the helical turn 112p or 112d. As shown in FIGS. 2A and 2B, the circumferential members 110p and 110d at the distal and proximal ends of the stent that can define a plane orthogonal to the longitudinal axis 102.

In FIGS. 3A and 3B, the circumferential rings define a plane orthogonal to the longitudinal axis 102 when the circumferential member 110p or 110d includes a circumferential ring 111p or 111d and a helical turn 112p or 112d. Alternatively, the ends of the stent can define other angles with respect to the longitudinal axis.

One or more of the circumferential members 110p or 110d can be flared. That is, a diameter at an end of the stent 100 is greater than a diameter defined at the direct connection of the circumferential member 110p or 110d and the helical element 120. For example, circumferential members 110p and 110d at both ends of the stent can be flared.

Optionally, apices of the circumferential ring 111p or 111d can be out of phase with apices of the helical turn 112p or 112d by about a half of wave period and the number of apices is equal. This can provide, for example, a peak to valley arrangement of apices in the circumferential member 110p or 110d. The helical turns of the helical element and the undulated helical turn of circumferential member can have constant and identical amplitude throughout the winding of the helical body of the stent.

In FIGS. 2A and 2B, the lengths of the closed cell connectors 118 vary. The lengths of the closed cell connectors 118 can uniformly increase along a circumferential direction of stent. Alternatively, the lengths of closed cell connectors 118 need not uniformly increase. For example, the closed cell connectors 118 can be placed at various locations between the undulations 107 of the helical turn 112p or 112d and the circumferential ring 111p or 111d, which will vary their lengths accordingly.

The widths of the closed cell connectors 118 can be varied. For example, in FIGS. 3A and 3B, the widths of all but one of the closed connectors are substantially the same. The shortest of the closed cell connectors joins two struts 115 that form the apex 114 of the circumferential ring 111p or 111d, and the last strut 117 of the apex 116 of the helical turn 112p or 112d. That closed cell connector can have a greater width than the other closed cell connectors 118, and can, for example, have a width approximately twice that of the other closed cell connectors.

Individual closed cell connectors 118 also can have variable widths. In FIG. 4C, the shortest closed cell connector 118 has a variable width. A portion of the length of that closed cell connector can be narrowed to provide a notch 119. The shown notch is directly adjacent to the apex of the adjoining circumferential ring 111p or 111d and can have length and width that is approximately equal to the width of apex junction as shown in FIG. 4A, although these parameters can also be varied beyond the width of the apex junction. That notch can be provided anywhere along the length of that closed cell connector, however. The notch can act as a hinge and facilitate bending at that point, or can reduce stresses and strains around the area when the stent is deformed. Alternatively, bending or stress/strain relief can be facilitated by other means, such as by varying the thickness of the strut locally at that point. Exemplary dimensions of aspects of the circumferential ring are shown in Table 1 below.

TABLE 1

Exemplary Closed Cell Connector Dimensions

| Measurement | Approximate Dimension (millimeters) |
|---|---|
| Length (shortest closed cell connector) | 0.4 |
| Length (longest closed cell connector) | 3.0 |
| Incremental Length Increase (closed cell connector) | 0.3 |
| Width (closed cell connector) | 0.1 |
| Length (notch) | 0.4 |
| Width (notch) | 0.1 |

In FIGS. 3A and 3B, the lengths and widths of the axial connectors 125 are shown to be substantially uniform throughout the stent. The lengths and widths of axial connectors 125, however, can vary. For example, the axial connectors 125 can be placed at various locations between the undulations 106 of the adjacent helical turns, which will vary their lengths.

The number of axial connectors 125 in the stent is variable. Two to six axial connectors are provided per helical turn, with a ratio of about 2.5 to 2.75 axial connectors per helical turn is shown in FIGS. 2A, 2B. The axial connectors 125 can be connected between adjacent apices of the undulating helical turns. Optionally, the axial connectors 125 in one helical turn pair, 121p-122, can be offset from the axial connectors 125 in the immediately adjacent helical turn pair. The placement of axial connectors, while offset in the immediately preceding and/or following helical turn pairs, can remain in the same longitudinal arrangement in the alternating pairs (see FIGS. 2A and 2B), every second helical turn pair. For example, in a helical turn pair 112p-121p, the axial connectors 125 have a specific offset arrangement. The axial connectors 125 in the immediately adjacent helical turn pair can have the same offset arrangement. The arrangement maintains the axial bending flexibility of the stent in virtually all directions. Other axial connector placements are also envisioned.

In FIGS. 3A and 3B, the axial connectors 125 extend between peaks and valleys. Between about two and six axial connectors 125 can be provided per helical turn to maintain flexibility. The placement of the axial connectors 125 in the stent body 101 can be varied from distal to proximal end (left to right in FIG. 2A or 3A). For example, some of the axial connectors 125 can be offset by about half an undulation period as compared to other of the axial connectors 125 of the stent body 101. This can help to avoid numerous four-strut junctions between the helical element 120 and the circumferential member 110d and to maintain the axial bending flexibility of the stent in virtually all directions.

Figure 6A:
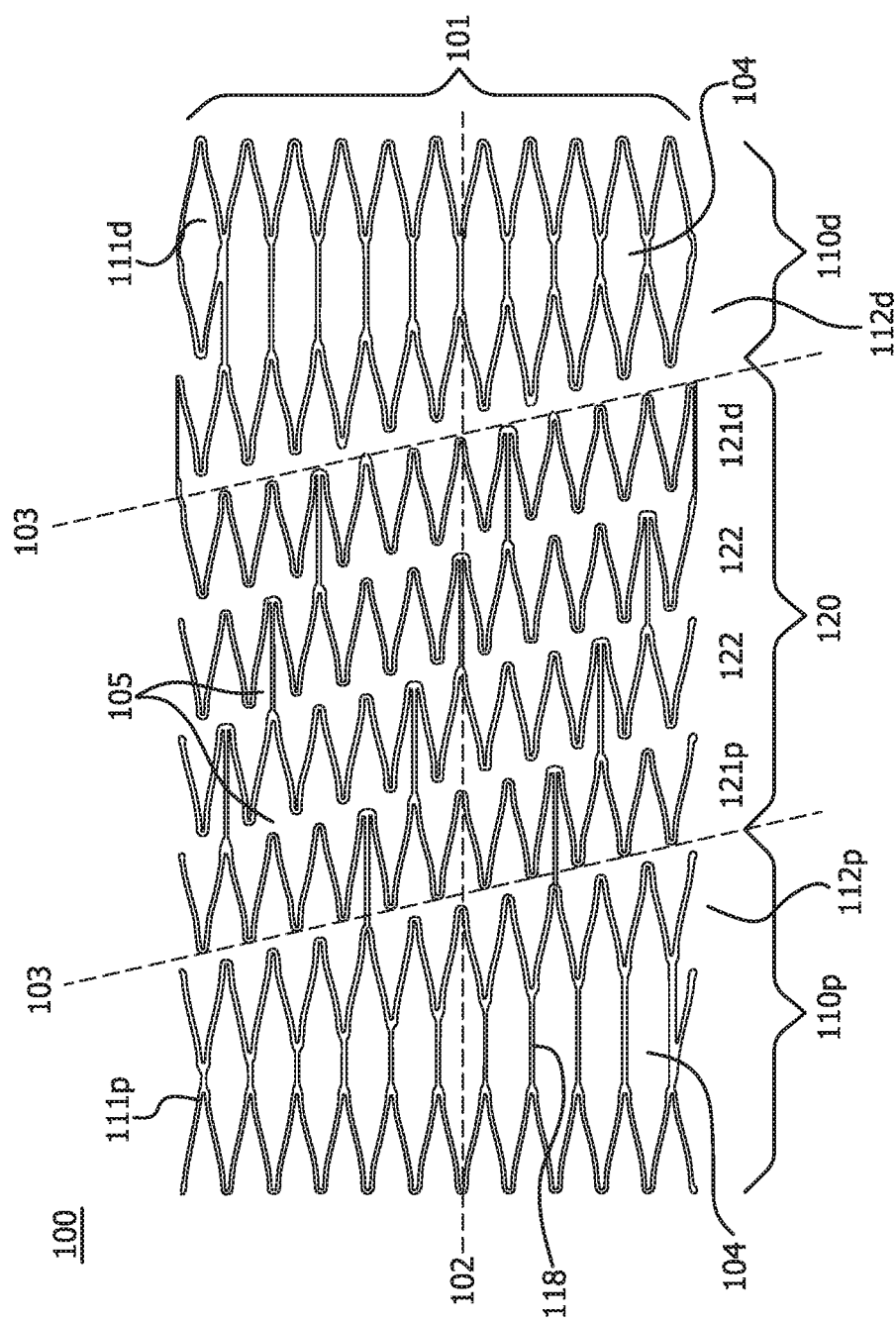
FIGS. 6A-6B are plan views of a stent (full circumference shown), which illustrates an interrelationship between circumferential members and a helical element of different length in a stent with eleven distal and eleven proximal facing apices per turn.
Figure 6B:
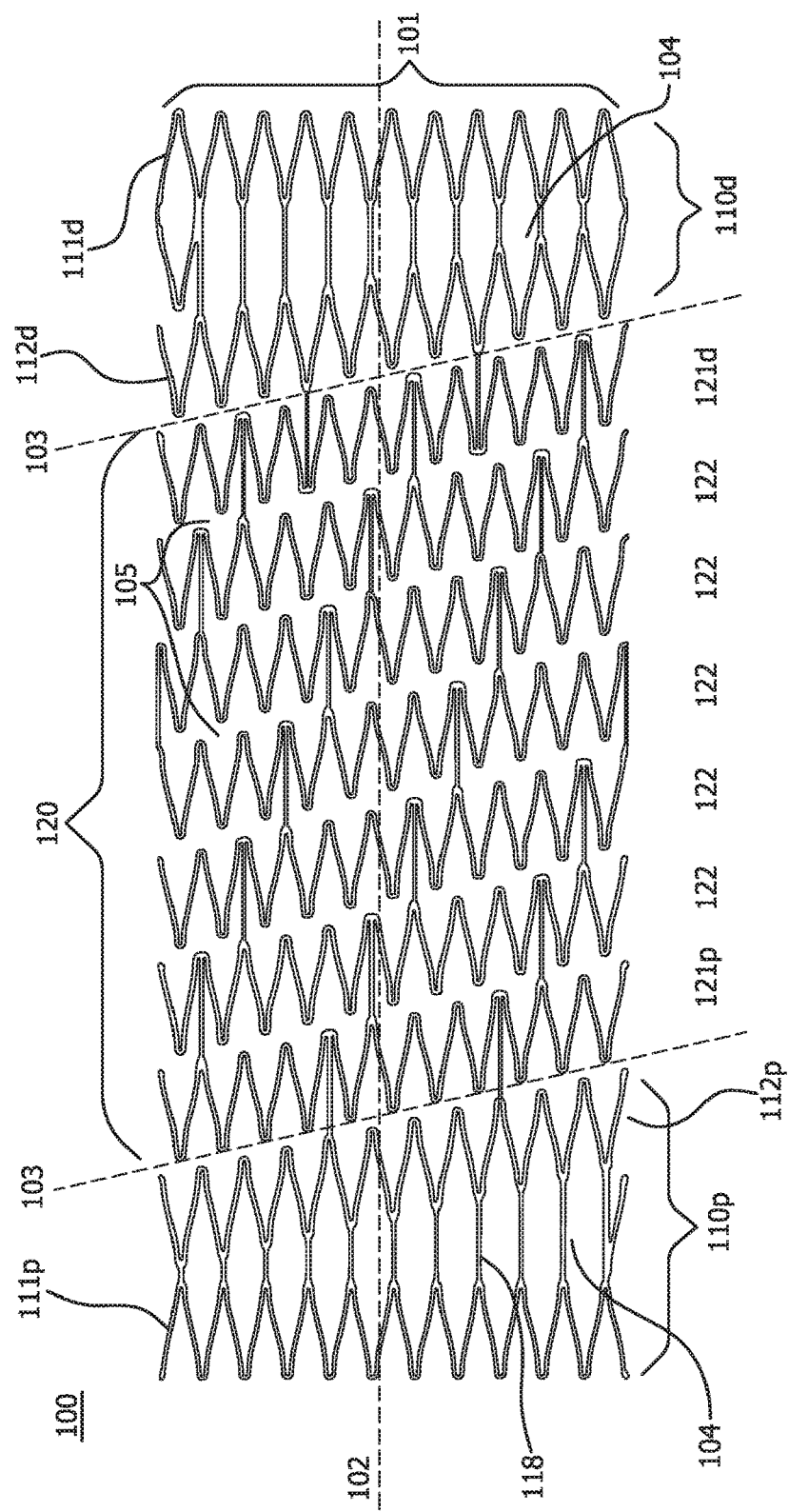
Figure 9:
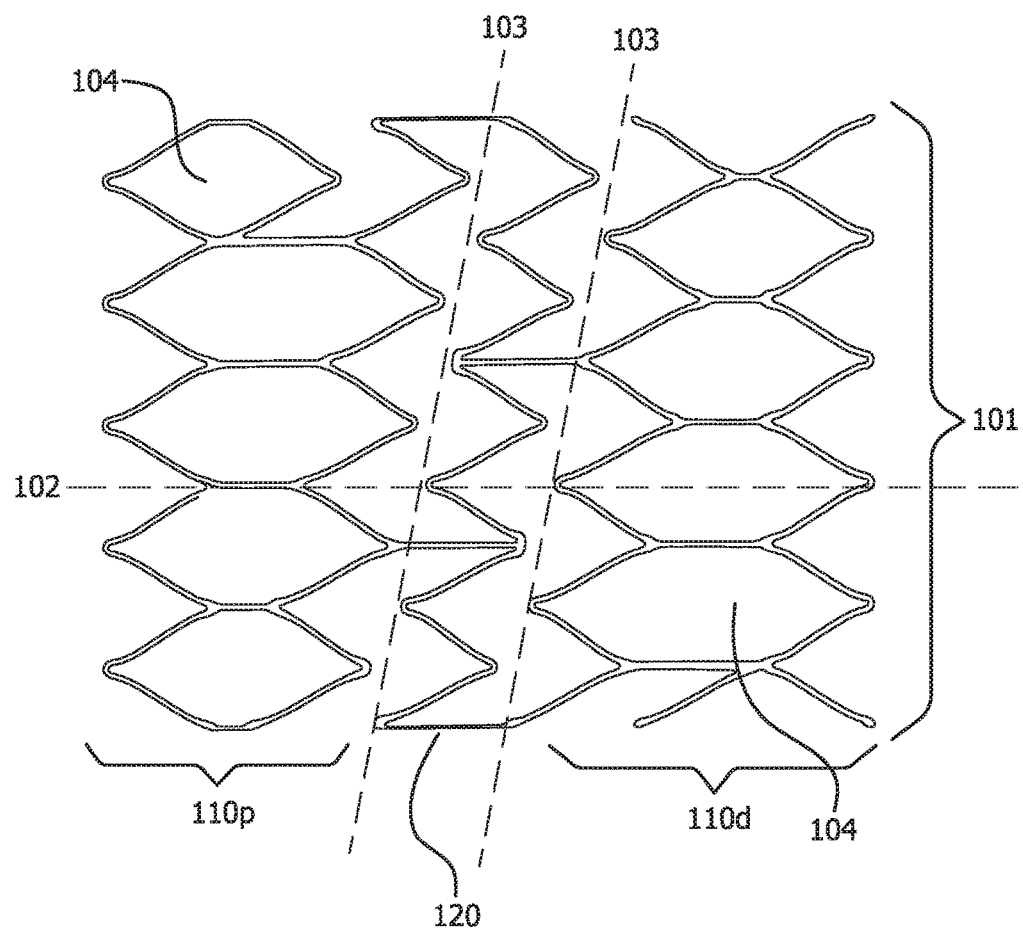
FIG. 9 is a plan view of a stent.

As illustrated in FIGS. 2A and 2B, the exemplary stent 100 defines the circumference of the stent body 101 by 10 distal facing apices ("10-apices") or, as illustrated in FIGS. 6A and 6B, by 11 distal facing apices ("11-apices"). For example, a smaller diameter stent can be a "10-apices" design with a deployed diameter of about 5 to 8 mm. A stent can have an undulating helical element 120 that comprises about one helical turn or a portion of one helical turn such as about ⅘, ¾, or ½ of a helical turn. An example of such a stent is shown in FIG. 9. The stent can have a deployed diameter of about 3 mm to about 6 mm, including about 3 mm, 3.5 mm, 4 mm, 4.5 mm, 5 mm, 5.5 mm, and 6 mm. Such a stent can have a length of about 15 mm and an insertion, pre-deployed diameter of about 1.0 mm to about 2.3 mm. A larger stent can be an "11-apices" design with a deployed diameter of about 9 to 10 mm. However, 6-, 8-, 9-, 12-, 13-, 14-, 15-, 16-, 18- and more apices are also envisioned and encompassed.

The number of closed cell connectors 118 depends on the number of apices in the stent body. In FIGS. 2A and 2B, there are ten closed cell connectors 118. In FIGS. 6A and 6B, there are eleven closed cell connectors 118. Increasing the number of closed cell connectors can increase the axial stiffness and columnar strength of the distal and proximal undulating circumferential members at the ends of the stent 100. This can decrease the overall tendency for the stent 100 migration along the vessel lumen and further reduces, for example, the tendency of the stent to either move into the site of the aneurysm or follow the path of the expanded vessel. If buckling occurs, the closed cell and axial connectors 118, 125, have a tendency to maintain axial spacing of the helical turns at their connection points, act as springs in this situation, store mechanical energy which then acts to restore the stent to an unbuckled state.

Exemplary dimensions of aspects of the undulating helical element are shown in Table 2 below:

TABLE 2

Exemplary Undulating Helical Element Dimensions

| Measurement | Approximate Dimension (millimeters) |
|---|---|
| Length (short strut) | 2.6 |
| Length (long strut) | 2.9 |
| Strut Width | 0.1 |
| Length (axial connector) | 3.1 |
| Width (axial connector) | 0.1 |
| Radius (apex) | 0.2 |
| Width (apex) | 0.2 |

Figure 5:
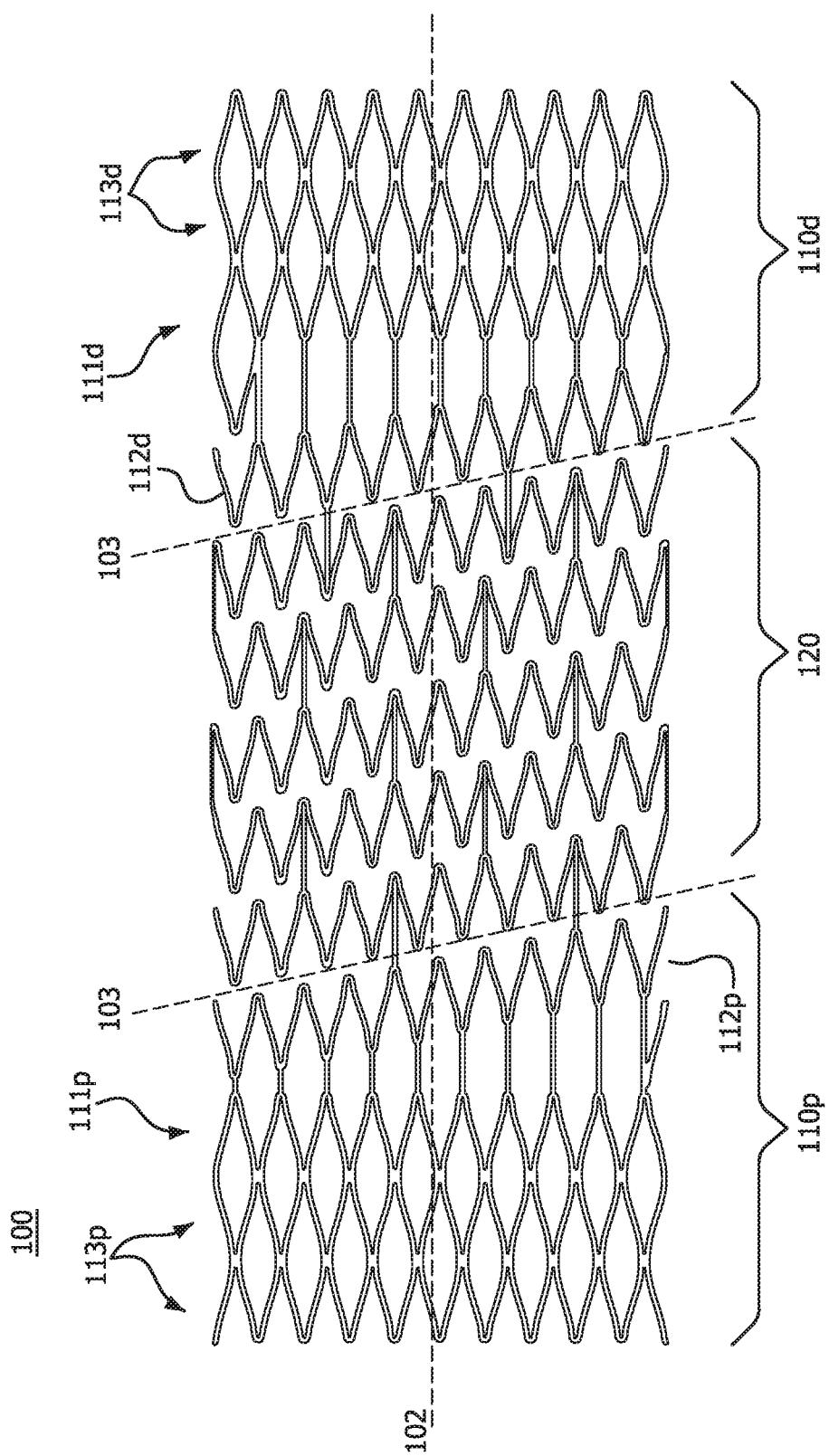
FIG. 5 is a plan view of a stent (full circumference shown) with several circumferential rings in a circumferential member.

FIG. 5 shows a variation of the circumferential members. The circumferential member is provided with additional circumferential rings 113$p$ or 113$d$ at the ends. For example, in FIG. 5, the additional undulating circumferential rings are shown as 113$p$ and 113$d$. The number of circumferential rings 111$p$ and 113$p$, or 111$d$ and 113$d$ at the distal and proximal ends can be the same or different.

The stent 100 can be formed from a wide variety of materials or combinations of materials, including metals and plastics. Among metals that can be used are stainless steel, titanium, tantalum, alloys such as Elgiloy® and Phynox® spring alloys, 316 stainless steel, MP35N® alloy, and Nitinol nickel-titanium alloy. Super-elastic versions or shape memory versions of the mentioned alloys can also be used. One can use metals that resume their original shape after being deformed to such a degree that an ordinary metal undergoes permanent deformation. Use of nitinol alloys can impart the self-expanding characteristic to the stent. In such a nitinol stent, the phase behavior of the material can be selected and the stent treated so that the stent has a tendency to transform from the insertion configuration to deployed configuration when unconstrained at body temperature. For example, the active $A_f$ (austenitic transformation finish) temperature for nitinol of the completed stent assembly, as ready for intended use, can be less than about 35° C., be between about 0° C. and about 25° C., or be between about 10° C. and about 17° C., as determined by a bend and free recovery test known in the art (see ASTM standard no. F2028-01).

Among plastics useful for fabricating the stents are PTFE, other fluoropolymers, or other plastics (such as PET). Among resorbable materials polymers or copolymers possessing one or more of the following monomeric components: glycolide (glycolic acid); lactide (d-lactide, l-lactide, d,l-lactide); trimethylene carbonate; p-dioxanone; caprolactone, hydroxybutyrate, hydroxyvalerate. These identified materials are exemplary and any material suitable for implantation can be used.

Any technique that produces a stent with the required characteristics can be used. For example, the stents can be cut from a continuous tube of material into the desired pattern, such as through use of a laser. The stents can also be constructed by various known techniques such as machining, chemical etching, laser ablation, die-cutting, plasma etching, stamping, water jet cutting or any other suitable means as long as the required stent structure can be achieved. The stents can also be formed from a flat sheet of material that is cut into the desired pattern and then bonded together to form a tube having a seam. Finally, the stents can be constructed from wires or ribbons that are formed into the desired shapes and then bonded together, for example by welding, into the final pattern.

Coverings can be provided for the stent. The use of coverings in combination with the stent can help, for example, to (1) minimize or at least reduce the risk of introduction of emboli into a bloodstream, (2) resist tissue encroachment into the lumen defined by the stent, and (3) reduce pressure on a weakened part of a blood vessel to reduce the risk of vessel rupture. Coverings can be made from continuous materials with no holes visible without magnification.

Figure 7A:
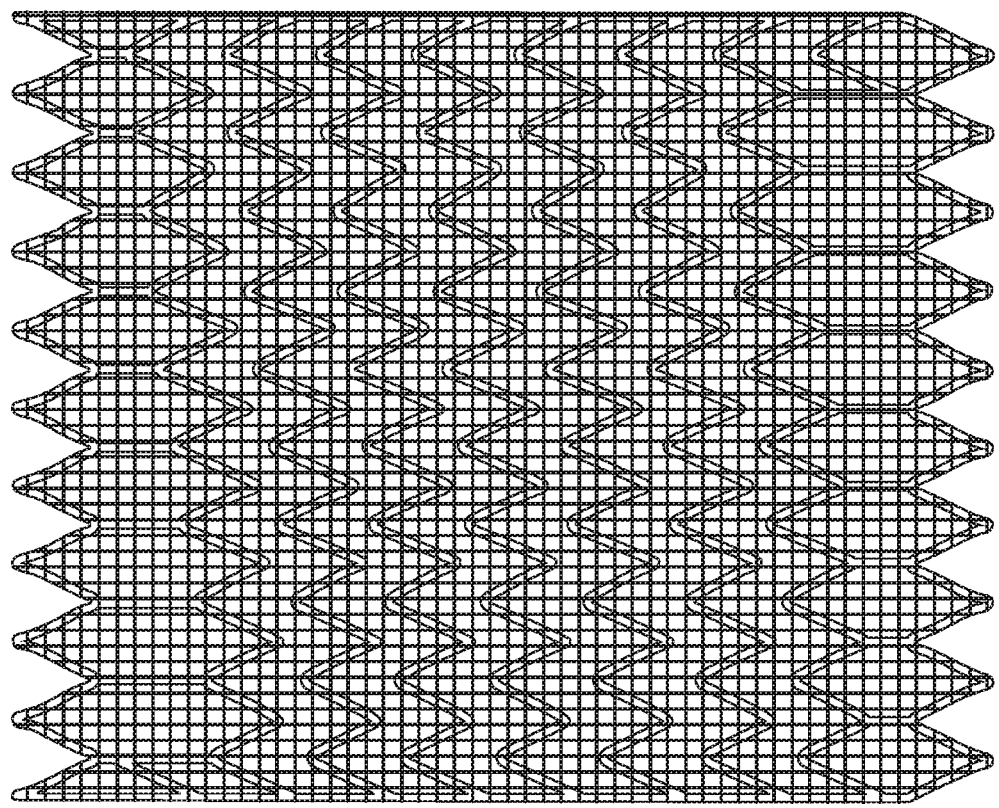
FIG. 7A is a plan view of the stent (full circumference shown) illustrated in FIG. 2A with a square-shaped lattice covering.
Figure 7B:
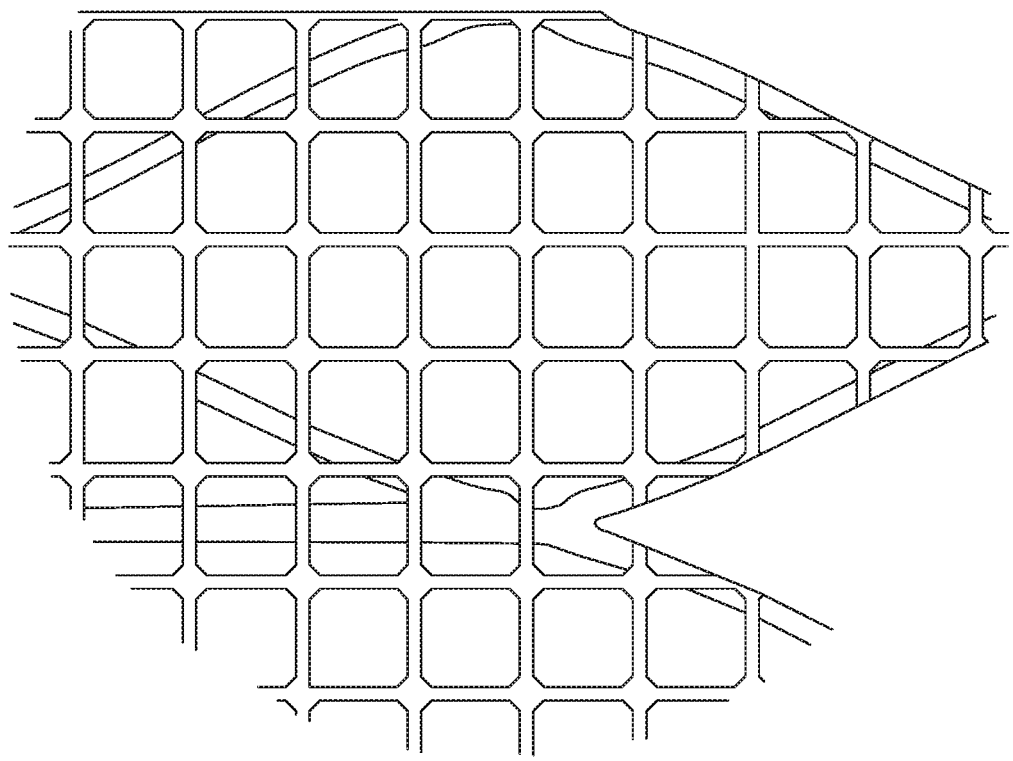
FIG. 7B is a close-up view of the stent illustrated in FIG. 7A.
Figure 7C:
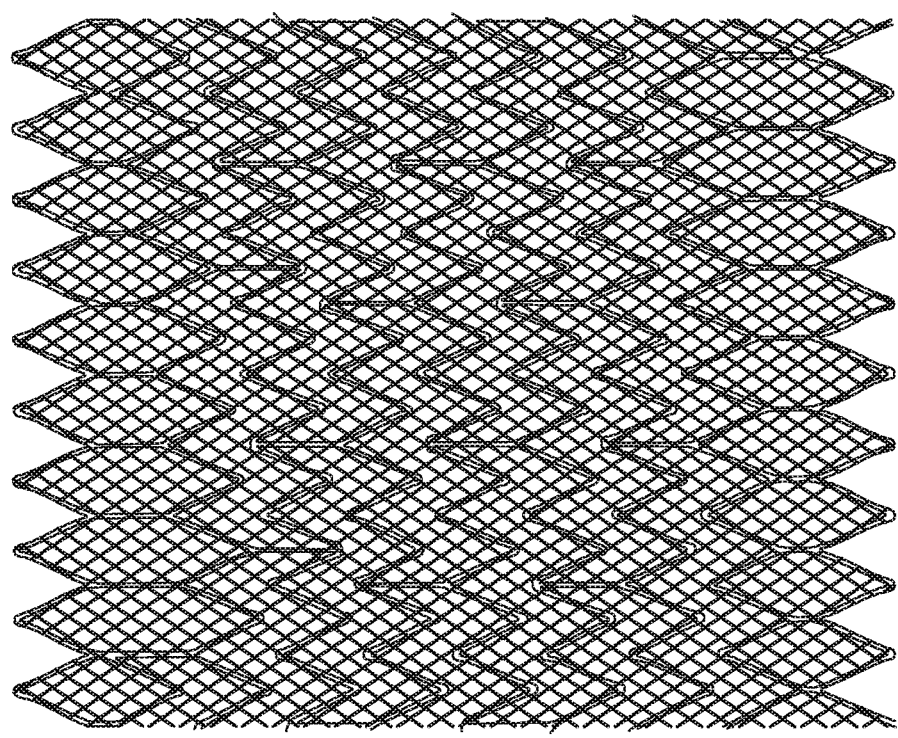
FIG. 7C is a plan view of the stent (full circumference shown) illustrated in FIG. 2A with a diamond-shaped lattice covering.

Additionally, FIGS. 7A and 7C illustrate two kinds of other coverings, which can be termed to be lattices. These lattices are unitary structures. A series of interconnected, continuous segments define one or more patterns of openings in the lattice. The width of the lattice segments ranges between about 0.02 mm and about 0.2 mm, between about 0.02 mm and about 0.1 mm, or about 0.05 mm. The thickness of the lattice segments ranges between about 0.02 mm and about 0.2 mm, between about 0.02 mm and about 0.1 mm, or about 0.05 mm. The lattice opening size is the diameter of the largest inscribed circle, and ranges between about 40 µm and about 1 mm, between about 50 µm and about 800 µm, between about 100 µm and about 750 µm, or between about 200 µm and about 500 µm. The lattice opening size can be the size of the smallest kerf width of a laser. A lattice opening for use in an application such as aneurysm exclusion can be between about 10 µm and about 40 µm, between about 12 µm and about 30 µm, or between about 15 µm and about 20 µm.

The lattice openings can be arranged in various regular and irregular patterns to provide diametrically stable functionality. The openings can have various shapes, such as triangles, squares, diamonds, parallelograms, hexagons, circles, or any other geometric shape, or combinations of shapes. FIGS. 7A and 7C show illustrative square and diamond-shaped openings, respectively.

The square-shaped lattice of FIG. 7A has a series of continuous longitudinal segments that extend in a direction that is substantially parallel to a longitudinal axis of the stent, and a series of continuous circumferential segments that extend in a direction that is at an angle approximately transverse to the longitudinal axis of the stent. In FIG. 7A, the square-shaped openings have four equal or substantially equal sides and its interior angles are all at or approximately right angles (90°).

The arrangement of the square-shaped lattice of FIG. 7A can provide longitudinal segments with substantially constant length in an insertion or constrained configuration (when the stent has a reduced profile), and in a deployed configuration (when the stent has an enlarged profile greater than the insertion profile). For example, as compared with overall length of longitudinal lattice segments in the deployed configuration, the longitudinal segments of the lattice can have lengths ±5% in the insertion configuration, ±4% in the insertion configuration or ±2% in the insertion configuration.

Alternatively, the lattice covering can have parallelogram-shaped openings. Continuous longitudinal segments extend in a direction that is substantially parallel to the longitudinal axis of the stent. Continuous circumferential segments extend at an angle with respect to the longitudinal axis that is greater than 0° and less than about 90° with respect to the longitudinal axis. For example, the circumferential segments can be oriented at an angle of about 45° with respect to the longitudinal axis. Such a parallelogram-shaped lattice can be positioned with respect to the stent so that one or more of the longitudinal segments extend along the length of the closed cell connectors.

Further, the lattice covering can have diamond-shaped openings as shown in FIG. 7C. Two sets of continuous circumferential segments extend at different angles with respect to the longitudinal axis of the stent. For example, a first set of the circumferential segments is oriented at an angle of about 45° with respect to the longitudinal axis, while a second set of the circumferential segments is oriented at an angle of about −45° and about −90° with respect to the longitudinal axis. In the lattice depicted in FIG. 7C, there are no longitudinal segments.

Yet still more lattice opening shapes can be obtained, such a triangles, or trapezoids, with additional lattice segments. For example, the lattice can have two sets of circumferential segments, as well as longitudinal segments. One set of the circumferential segments can be oriented at an angle of between about 45° and about 90° with respect to the longitudinal axis, while a second set of the circumferential segments can be oriented at an angle of between about −45° and about −90° with respect to the longitudinal axis.

Longitudinal and/or circumferential lattice segments can be positioned to extend along one or more stent struts. For example, in FIG. 8B, longitudinal segments of the square-shaped openings extend along one of the closed cell connectors of the circumferential member, and are longitudinally aligned with it. The number of longitudinal segments of the lattice covering can be the same as or greater than the number of the closed cell connectors in each of the circumferential members. One, some, or all of the longitudinal members can be joined with the closed cell connectors. Similarly, other shaped openings of the lattice can be aligned so that one or more sides extend along the length of one or more connector struts within the stent.

Figure 8A:
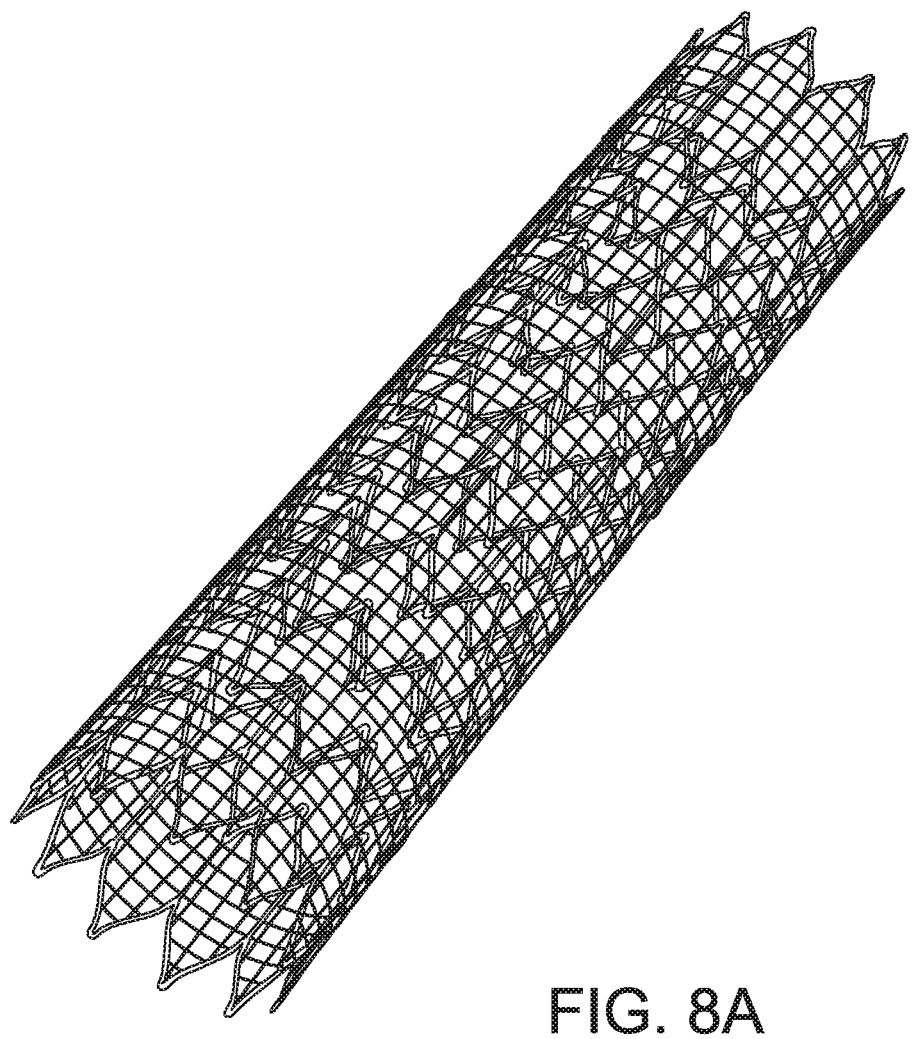
FIG. 8A is a full view of a stent with a square-shaped lattice covering.
Figure 8B:
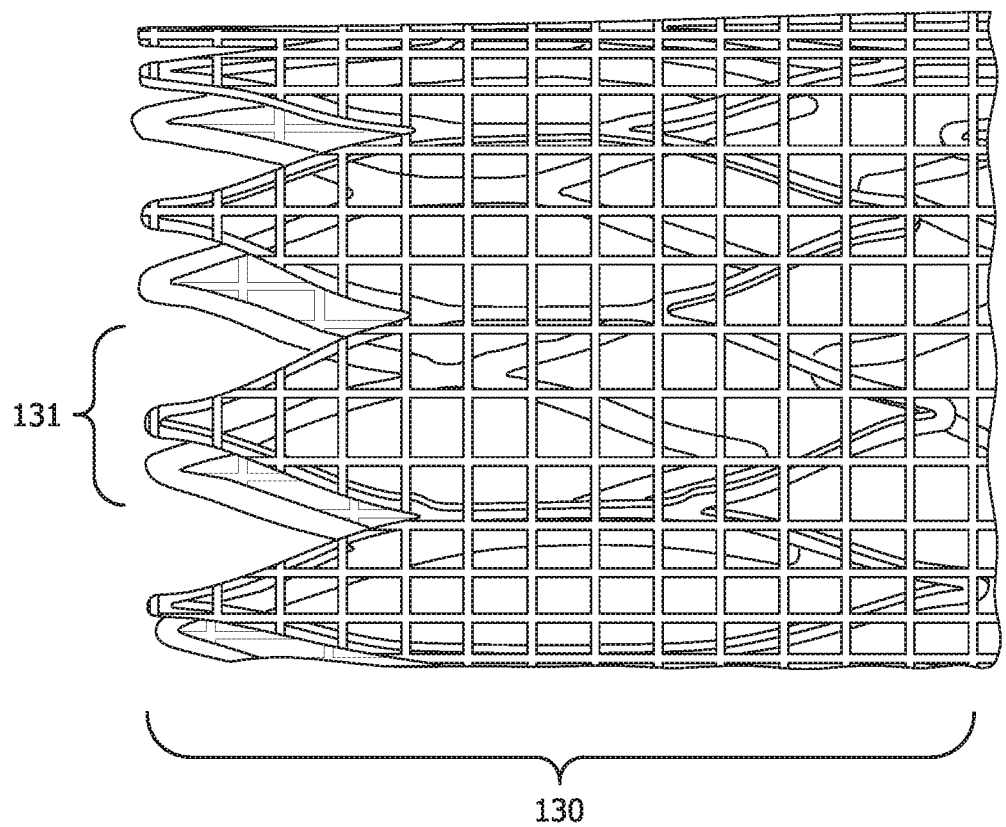
FIG. 8B is a close-up view of a stent at one of its ends with a square shape lattice.
Figure 8C:
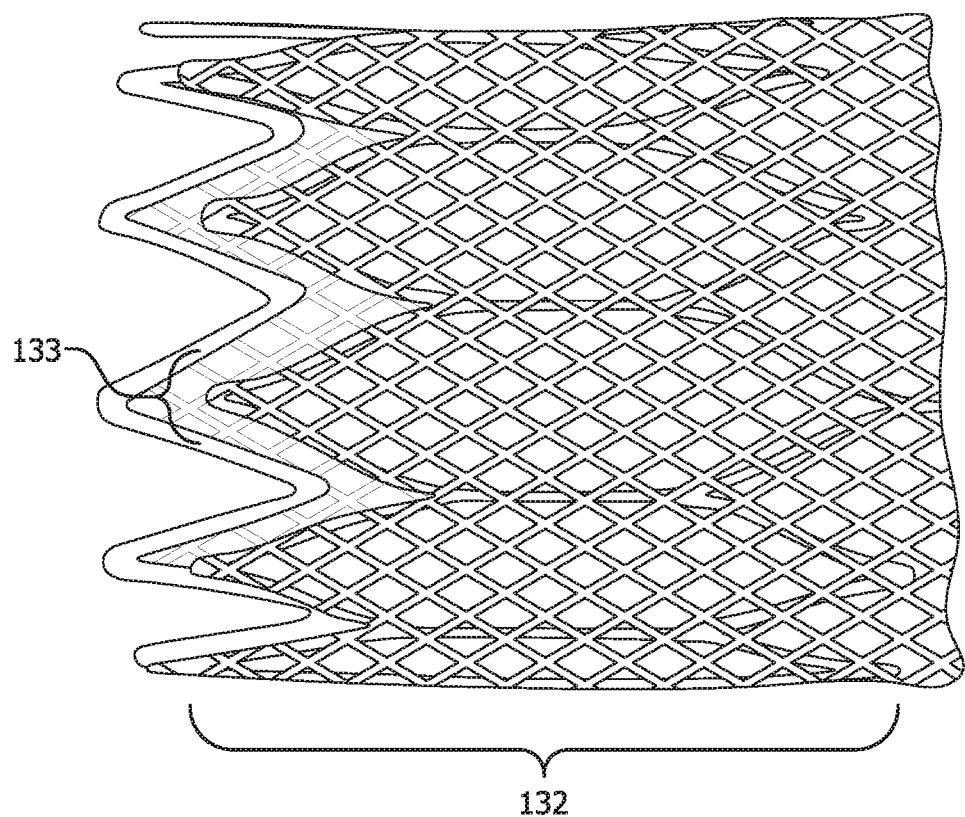
FIG. 8C is a close-up view of a stent at one of its ends with a diamond shape lattice.

The number of attachments between the stent and the lattice covering can be varied depending on various factors, such as the size of the stent openings, the size of the lattice openings, and the orientation of the lattice with respect to the stent. In FIGS. 8B and 8C, the closed cells 130 of the stent have a larger dimension along the longitudinal axis, and a shorter dimension transverse to the longitudinal axis. In FIG. 8B, the square-shaped lattice covering is oriented with fewer lattice openings across the larger dimension of the closed cell 130, and an equal or fewer lattice openings across the smaller dimension of the closed cell 131. In FIG. 8C, the diamond-shaped lattice covering is oriented with more lattice openings across the smaller dimension of the closed cell (133) than in FIG. 8B.

A substantially uniform lattice opening pattern is shown in FIGS. 7A, 7B and 7C. In those lattices, the size and shape of the openings is substantially uniform throughout. However, the lattice opening pattern also can be irregular. Lattice openings can be provided in one portion and not in the balance of the lattice. For example, a first arc of the lattice can have openings along the entire length of the lattice while a second arc opposite of the first arc is substantially without openings. Alternatively, the lattice openings can be provided in along a spiral with respect to the longitudinal axis. Further still, the lattice can have a perfusion region within which the openings are provided and an excluding region devoid of openings, thus, configured to allow orientation of the perfusion region to be determined endovascularly.

Alternatively, the lattice openings can have several patterns. The openings of similar size and shape can be grouped together to have at least two sets of openings with each set having a predetermined size and shape, or uniformly distributed throughout the lattice. For example, lattice openings corresponding to the circumferential members can be square-shaped as depicted in FIG. 7A, while the lattice openings corresponding to the helical element can be diamond-shaped as depicted in FIG. 7C.

Alternatively, the lattice can have three sets of openings distributed along the length of the lattice, one at the proximal end, one at the distal end and one in-between. The openings of the proximal set, for example, can have diamond-shaped openings with a nominal diameter of about 300 μm as measured by the largest inscribed circle. The openings of the distal set, for example, can also have diamond-shaped openings but with a nominal diameter of about 500 μm as measured by the largest inscribed circle. On the other hand, the openings of the central set, those that span between the proximal and distal sets, can have squared-shaped openings with a nominal diameter of about 100 μm as measured by the largest inscribed circle. Other permutations, sets, and groupings are also envisioned. For example, in addition to the square or diamond-shaped lattice openings, one or more large oval openings adapted to allow for side branch perfusion can be provided.

The lattice can be produced by laser cutting, such as a $CO_2$ laser, from a longitudinally wrapped tube of, for example, six layers of biaxially-oriented film made from one suitable cover material or from a combination of suitable cover materials to produce a unitary structure, not woven. Such a lattice could have a nominal thickness between about 10 μm and about 250 μm, between about 20 μm and about 60 μm, or between about 35 m and about 50 μm. Other films can be used together with the biaxially-oriented films or in place of them to form the lattice. For example, uniaxially-oriented or multiaxially-oriented films can be used. These films can be wrapped longitudinally as described above, or can be wrapped in other configurations. For example, the films can be helically wound to form the tubular structure. Other methods of lattice preparation are also envisioned in accordance with the procedures described in U.S. Pat. Pub. No. 2008/0119943 to Armstrong et al., or U.S. Pat. No. 7,306,729 to Bacino et al., the entire disclosures of which are incorporated herein by reference. Alternatively, a lattice can also be formed from a fiber by techniques such a knitting, weaving, or crocheting.

Conformability of the stent with and without the lattice can be measured according various known test methods. For example, ISO 25539-2 (2008) describes one protocol for assessing the ability of medical devices to conform to vessel walls and is incorporated in and constitutes a part of this specification. Most generally, the test method measures the smallest radius of curvature that a stent can withstand without kinking. A more conformable stent will have greater ability to conform to bends having a smaller radius of curvature without kinking, and a less conformable stent will have a lesser ability to conform to such bends without kinking.

Flexibility of the stent with and without the lattice can be assessed by a three-point bend test on deployed stents. One method for such testing is set forth in ASTM F2606-08, the entire disclosure of which is incorporated herein by reference. Most generally, after the stent is placed into a specific three-point bend fixture, the amount of force required to bend the stent is measured. The resulting load-deflection curves can be used to assess flexibility of stents. A more flexible stent will have greater ability to bend at lower forces, and a less flexible stent will have a lesser ability to bend at lower forces.

The stent and the lattice can be sized to be the same or different. The lattice covering shown in FIGS. 7A, 7C, 8A and 8B does not notably constrain the stent, and for example, the stent has an outer diameter of about 8 mm, and the lattice has an inner diameter of about 8 mm.

Alternatively, however, the lattice can resist full expansion of the stent, depending upon lattice geometry and material chosen. This can be achieved by over-sizing the stent with respect to the lattice covering. The stent can have an outer diameter that is oversized with respect to the lattice covering in an amount of about 10% to about 100%, between about 20% and about 70%, or between 30% and about 50%. For example, the self-expanding stent can have an outer diameter of about 10 mm, and the lattice can have an inner diameter of about 8 mm. An effect of oversizing the stent as compared to the lattice (in this example to about 20%) is to provide a final self-expanding device that resists forces tending to collapse the deployed stent. The amount of force needed to reduce the diameter of the deployed stent is higher when an oversized self-expanding stent is used as compared with the same stent that is not oversized.

In addition to oversizing the stent as compared with the lattice, the lattice can be made from a distensible material. A distensible material for the lattice can be made according to various known techniques, such as in accordance with the procedures described in U.S. Pat. Nos. 4,877,661 and 5,026,513 to House et al., the entire disclosures of which are incorporated herein by reference. The lattice made from distensible material can have a rapid recovery of greater than about 5.5%, greater than about 15%, or greater than about 30%. For example, the stent can be sized to have an outer diameter of about 8 mm, and the distensible lattice can be sized to have an inner diameter of about 6 mm.

Figure 11C:
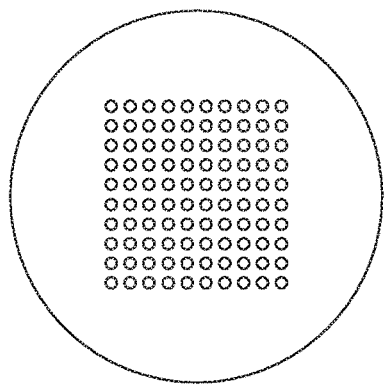
FIG. 11C is a partial close-up view of a lattice after a micro-catheter is advanced through a lattice opening.
Figure 11B:
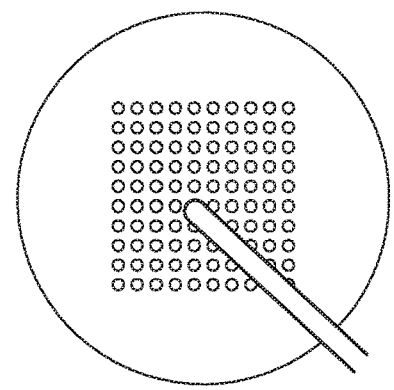
FIG. 11B is a partial close-up view of a lattice as a micro-catheter is advanced through a lattice opening.
Figure 11A:
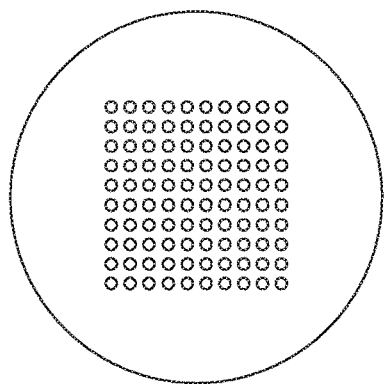
FIG. 11A is a partial close-up view of a lattice prior to a micro-catheter advancing through a lattice opening.

A lattice covering can stretch or deform when advancing a catheter or other tool from a deployment system through its sidewall to allow crossing for deployment of a side branch device or other device. FIG. 11A is a partial view of a lattice covering prior to micro-catheter advancement. FIG. 11B is a partial view of the lattice with a micro-catheter advancing through one of the lattice openings and showing the opening deforming to take the shape of the outer diameter of the micro-catheter. FIG. 11C is a partial view of the same lattice in FIG. 11B after the micro-catheter is removed and shows that the lattice opening has substantially returned to its original size and shape. The lattice would substantially return to its structure, size and shape once the side branch or additional device is deployed and that deployment system removed from the lattice.

A lattice covering can be formed from longitudinal strips of any of the cover materials described herein including by bonding or weaving into a basket weave, mesh, or lattice pattern.

Figure 12A:
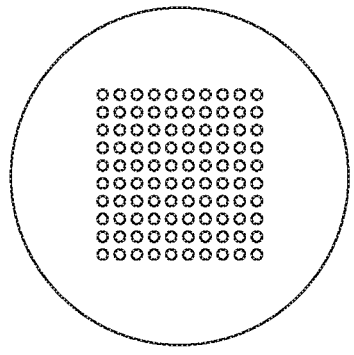
FIG. 12A is a partial close-up of a lattice.
Figure 12B:
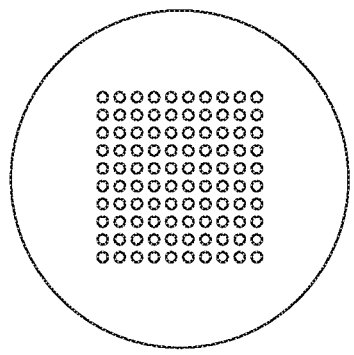
FIG. 12B is a partial close-up of a lattice.
Figure 12C:
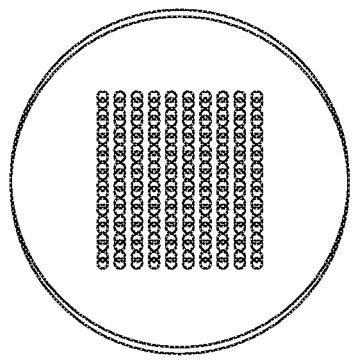
FIG. 12C is a partial close-up of the lattice of 12B applied to the lattice of 12A.
Figure 12D:
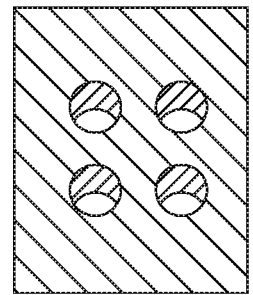
FIG. 12D is a partial close-up of the lattice openings in the lattice of FIG. 12C.

Optionally, a stent can be covered with multiple layers of coverings. A lattice can be formed by two or more layers of lattice coverings. Two or more layers can be bonded together with openings aligned or offset. One or more of the layers can have elastic properties. Two lattice coverings as shown in FIGS. 12A and 12B can be layered such that the openings are offset or staggered as shown in FIG. 12C. The resulting open area, as shown in FIG. 2D, may provide smaller trans-mural porosity than may be achieved by utilizing a single lattice covering.

A lattice can be imbibed with PVA (polyvinyl alcohol) or other materials (e.g., gold, platinum/iridium, or the like) to aid the physician during imaging (e.g., ultrasound, fluoroscopy, MRI, or the like). A lattice can be imbibed with one or more therapeutic agents. The term "imbibed or imbibing" as used herein is meant to describe any means for at least partially filling a portion of the pores of a porous material such as ePTFE or the like. This can be done during manufacturing by, for example imbibing, or it can be done during catheter flushing which may imbibe or coat one or more therapeutic agents into or onto the lattice. Imbibing or coating of a therapeutic agent can result in release of the agent over time. One skilled in the art can select suitable therapeutic agents including without limitation: sirolimus, dexamethoasone, paclitaxel, phosphorylcholine, everolimus, or like agents. As used herein, a therapeutic agent can be a drug or other pharmaceutical product such as a non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, paclitaxel, etc. Where an agent includes a genetic therapeutic agent, such a genetic agent may include but is not limited to: DNA, RNA and their respective derivatives and/or components: hedgehog proteins, etc. Where a therapeutic agent includes a cellular material, the cellular material may include but is not limited to: cells of human origin and/or non-human origin as well as their respective components and/or derivatives thereof. Where the therapeutic agent includes a polymer agent, the polymer agent may be a poly-styrene-polyisobutylene-polystyrene triblock copolymer (SIBS), polyethylene oxide, silicone rubber and/or any other suitable substrate. In at least one embodiment the polymer agent can be biodegradable such as PLA, PLGA, etc. A therapeutic agent can also be a coating material as described herein.

A lattice can also be imbibed with an alginate. The alginate can be imbibed throughout the lattice or selectively to one or more portions of the lattice. The alginate can be cross-linked by delivering divalent or trivalent cations (for example, calcium) though a catheter or the stent delivery system to the stent delivery site. The cross-linked alginate portion of the lattice can be used to relieve pressure from weakened portions of a blood vessel (for example, to treat a cerebral aneurysm) or to occlude other openings or vessels adjacent to the sidewall of the stent. A lattice can be imbibed with calcium. An alginate can be delivered to the calcium imbibed lattice through the stent delivery system or by another catheter system to cause crosslinking on or in close proximity to the lattice. A stent with a calcium imbibed lattice can be placed over an aneurysm neck and then one can introduce the alginate through the lattice and into the aneurysm. While flowing through the calcium imbibed lattice, the alginate can react with the calcium to cause formation of a gel in the aneurysm sac.

In FIGS. 7A and 7B, the lattice is shown to be generally uniform. Alternatively, the lattice covering can be varied along its length. For example, the size of the openings, the orientation of the openings and their shapes need not be uniform throughout the lattice covering. A portion of the lattice covering can have square-shaped openings and another portion of the lattice covering can have diamond-shaped openings.

These coverings can be joined to the stent over all or over only a portion of the device length. The coverings can be joined intermittently. For example, a lattice covering can be joined only at the ends of the stent, at the closed cell portions of the stent, or only at the closed cell connectors. The covering can be on the outside of the stent elements; it can be on the inside of the stent; or it can be on both.

The attachment of the stent and the covering can be accomplished by mechanical means such as fiber, braiding a lattice into the stent, or discrete mechanical attachment points (clips, etc.). These components also can be bonded together through heat treatment (such as, sintering of the materials together) or through use of a wrap (for instance a tube, tape, or membrane) around the outside of the stent and cover (either continuous or discontinuous), that is adhered through either a thermoplastic or thermoset adhesive to the stent and cover. The covering also can be attached to the stent by adhering the two together through use of a suitable adhesive. Combinations of these methods also can be used. These methods and combinations of these methods can be used to attach the stent and covering while under inert gas conditions as commonly known in the art.

Among suitable biocompatible adhesives are thermoplastic adhesives such as fluorinated ethylene propylene (FEP), polyurethane, cyanoacrylate, thermoplastic fluoropolymer, including flouroelastomers such as those disclosed in U.S. Pat. No. 7,049,380 [TFE/PMVE], etc. Thermoset adhesives are also useful, such as silicone including room temperature vulcanizing (RTV) silicone.

For example, where the cover is a PTFE lattice; fluorinated ethylene propylene (FEP) can be used as an adhesive. Such a coating can be applied by various methods including extrusion over the covering, powder coating with powdered FEP that is subsequently melted to flow over the lattice surface, or running the covering through a bath of molten FEP optionally followed by pulling the covering through a die to achieve uniformity of the coating. Alternatively, the stent can be provided with a coating of adhesive such as by powder coating with FEP in a continuous or discontinuous fashion, or through use of an FEP wrap (for instance a tube, tape, or membrane).

A cover can be provided that allows the stent to be embedded within the cover material, such as through use of a silicone or other elastomeric material.

Covers can be coextensive with the length of the stent, as shown in FIGS. 7A-7C and 8A-8C, or they can be either longer or shorter than the stent. Covers can also cover only a portion of the stent, or can cover separately two or more portions of the stent. If multiple portions are covered, covers can also overlap on the stent.

Additionally, the stent, the covering or both can be provided with additional treatment or therapeutic agents, such a drugs, radiation, radiopaque markers or coatings, or other agents to enhance visualization in-vivo. For example, various coatings can be provided on all or some of the stent surface, the covering or both. Suitable coating materials include fluoroelastomer, ceramic, silicone, polyethylene, carbon, gold, heparin, hydrogel, lubricious coatings, antibiotics, anticoagulant agents, anti-inflammatory agents, antimetabolic agents, antimicrobial agents, antimigratory agents, antiplatelet agents, antiproliferative agents, antisense agents, cytostatic agents, nitric oxide releasing agents, pro-endothelial agents, selective gene delivery vectors, super oxide dismutases, super oxide dismutases mimics, vasoactive agents, and combinations thereof, such as, for example, actinomycin-D, ciclosporin, clobetasol, dexamethasone, estradiol, everolimus, heparin, paclitaxel, pimecrolimus, rapamycin, sirolimus, tacrolimus, and derivatives of these compounds. Coating materials can provide numerous benefits, including protecting the underlying stent material, providing a substrate for delivery of drugs or other therapeutic substances, isolating the stent material from interaction with surrounding cells, improving fluoroscopic visualization. Coatings can be applied in any material-appropriate manner, such as dip-coating, spray-coating, electro-deposit, or chemical vapor deposition.

Such a stent can be used to treat various body lumens, including, the aortoiliac, carotid, cerebral, coronary, hepatic, infrainguinal, mesenteric, renal, splenic, subclavian, and superior mesenteric arteries. Such a stent's configuration allows it to conform to the native anatomy of blood vessels or other body lumens, while also enhancing the stent's fatigue performance and crush-resistance.

For example, a stent as described herein can be used for treating stenosis in a carotid artery of a patient. A stent is provided having an insertion configuration with a reduced profile and a deployed configuration with an enlarged profile greater than the insertion profile. For example, the stent can be a nitinol stent which is capable of self-expanding to the deployed configuration when a constraint is removed. The stent has at least two spaced apart, undulating circumferential members, and an undulating helical element extending helically about the longitudinal axis, axially interposed between and directly connected to the circumferential members. The undulating helical element defines a plurality of open cells, and the circumferential member defines a plurality of closed cells. The stent is inserted into the vasculature of the patient. The stent is then positioned and deployed within the patient's carotid artery, for example, at a position where plaque has caused a narrowing of the artery.

The stent can be delivered by catheter. The stent can be radially compressed and placed within a sheath. The sheath can be subsequently mounted on a 5F (for 6-8 mm) or 6F (for 9-10 mm) introducer-sheath compatible delivery system. To aid visualization during delivery and deployment, one or more radiopaque markers can be integrated into the delivery system. For example, one radiopaque marker, such as $BaSO_4$, can be placed into the polymer used for the distal tip of the catheter. Another radiopaque marker, such as a platinum/iridium band, can be incorporated into the sheath material to indicate progression of the sheath retraction during stent deployment. Additionally, two markers, such as gold, platinum, or tantalum, can be placed adjacent to the proximal and distal ends of the compressed stent to aid in positioning.

Exemplary deployment systems that can be used in conjunction with the stents discloses herein include U.S. Pat. Nos. 6,139,572; 6,352,561 and 7,198,636 which are incorporated by reference herein.

Figure 10:
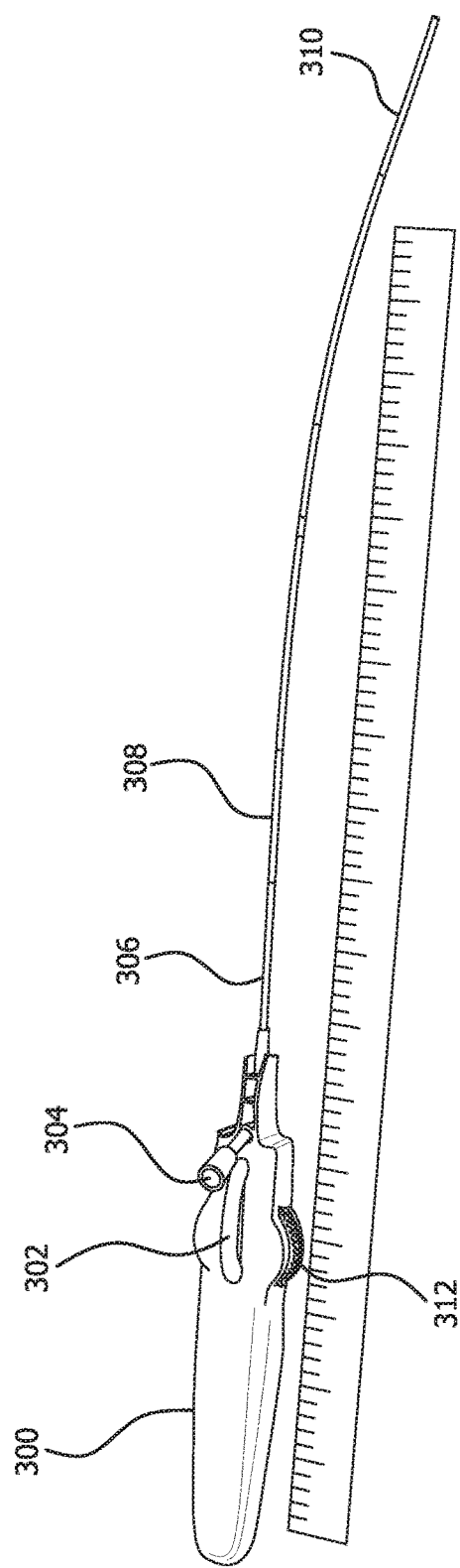
FIG. 10 is a full view of a delivery system.

Alternate deployment systems can be adapted for access in arteries or veins above the pelvis; for example, from the radial, brachial, and common carotid arteries. For carotid artery deployments, the access site arteries listed above are close to the carotid bifurcation and an alternate delivery system as shown in FIG. 10 can be used. The stent can be compressed and mounted on a delivery system as described previously. The common carotid artery can be punctured at a location just above the collarbone. In this instance, the distance from the puncture site to the carotid bifurcation is less than 20 cm. The use of a conventional carotid stent delivery system in this instance would leave a significant length of redundant catheter thus necessitating the use of an assistant to stabilize and deploy the stent. An alternate deployment system can allow a single operator. Any stent can be delivered with such a delivery system. An example of a stent that can be delivered with such a delivery system would be a self-expanding stent including stents described herein, stents having a high radial force upon delivery, stents with a small circular cell size between expanded metal struts, and/or stents designed to be deployed to a heavily calcified region of vasculature. A delivery system adapted for access from the radial, brachial and carotid arteries can range from about 15 cm to about 80 cm in length and can be no longer than about 45 cm (or about 60 cm or about 30 cm or about 20 cm) for ease of use and operation by one operator. As shown in FIG. 10, a delivery system can have a handle housing 300, a locking mechanism 302, flushing port 304, strain relief 306, catheter shaft 308, retractable sheath 310 covering stent, and a mechanism for operation of the deployment such as a thumb wheel 312.

In some instances, it may be beneficial to provide a covering on the stent. For example, a cover can provide a scaffold to reduce the risk of introduction of emboli being released into a bloodstream. A cover also can resist tissue encouragement into the lumen defined by the stent. Further, a cover can help to reduce pressure on a weakened part of a blood vessel, which in turn can reduce the risk of vessel rupture.

For example, for carotid applications, the stent with a lattice (see FIGS. 7A and 7B) can be useful for treating carotid stenosis. The lattice covered stent retains its flexibility and conforms to the anatomy, yet retains plaque due to a substantially smaller effective opening size of the lattice (as small as 0.04 mm).

The method for doing so includes several steps. First, a stent is provided as described above having at least two spaced apart, undulating circumferential members, and an undulating helical element extending helically about the longitudinal axis, axially interposed between and directly connected to the circumferential members. The undulating helical element defines a plurality of open cells, and the circumferential member defines a plurality of closed cells. Second, the stent is inserted into the patient while the stent is in an insertion configuration with a reduced profile. Third, the stent is moved through the patients vasculature and positioned with the portion of the carotid artery to be treated. Fourth, the stent is deployed so that it assumes an enlarged profile greater than the insertion profile. Alternatively, the stent can include a lattice covering to provide further emboli protection.

In this method, the stent and lattice are configured and positioned after deployment so that the stent provides scaffolding necessary to hold the artery open and ensure adequate blood flow, while the lattice in combination with the stent simultaneously provides plaque stabilization.

The lattice openings can further provide perfusion to a side branch vessel in this application when properly positioned. For example, a lattice can have a perfusion region with openings and an excluding region substantially without the openings. By determining the orientation of the perfusion region endovascularly, the lattice covered stent can be positioned so that the perfusion region allows side branch perfusion. Orientation can be determined by fluoroscopic visualization of one or more radiopaque markers incorporated within the lattice.

Also, a lattice covered stent can be used in conjunction with balloon catheters and/or guidewires, for example, to provide perfusion to a side branch vessel. After initially deploying the lattice covered stent as above, a balloon catheter can be endovascularly introduced into a one of the openings of the lattice, and expanded to distend or disrupt lattice covering. This allows endovascular modification of the size and shape of at least that one opening. Again, this can help to provide side branch perfusion among other uses.

These methods of using the stent disclosed herein are exemplary and not limiting. Further uses will be recognized by a skilled artisan.

EXAMPLE 1

A stent is prepared using a commercially-available medical grade nitinol tubing. The composition of the nitinol is selected so that the finished stent frame, prior to subsequent processing as described in examples 5 and 6 below, has an active austenitic transformation finish temperature of about 20° C. or less. The tubing is laser cut to remove material from the tubing and to provide a structure as shown in FIGS. 2A and 2B with 10 apices and a deployed diameter of about 8 mm, a thickness of about 0.15 mm. Slag, which can be formed during laser cutting of nitinol, is removed by mechanical or chemical techniques to provide a smooth exterior surface. The laser cut tube also is electropolished.

This self-expanding stent device is diametrically compacted at ambient temperature. Compaction is effected using a collet or iris type of diametrical compaction device, such as taught by U.S. Pat. No. 6,629,350. The compacted stent device is inserted directly from the compaction device into a length of capture tubing to retain the stent device in its compacted state.

EXAMPLE 2

The stent with 11 apices and 10 mm deployed diameter prepared in accordance with a configuration illustrated in FIGS. 6A and 6B and substantially as set forth in Example 1. This time, however, the self-expanding stent device is diametrically compacted at a reduced temperature of about −10° C.

EXAMPLE 3

A lattice of the type shown in FIGS. 7A and 8B with square-shaped openings is prepared. A mandrel is wrapped with an ePTFE film with a discontinuous FEP coating to a thickness of approximately 0.05 mm. The film-mandrel assembly is placed into an oven at 320° C. for 12 minutes to bond the layers. The assembly is removed from the oven and allowed to cool at room temperature to provide an ePTFE tube. Using a $CO_2$ laser, a pattern of regular square openings is cut into the tube. The openings are square-shaped with a size of less than about 0.5 mm. The width of the lattice segments is greater than about 0.05 mm (see FIG. 7B). The prepared square shaped lattice is placed in a convection oven set at 370° C. for 12 minutes. The material shrinks during heating to form squares that are approximately 0.5 mm diameter inscribed circle and lattice segments that are approximately 0.05 mm wide.

EXAMPLE 4

A lattice of the type shown in FIGS. 7B and 8C with diamond-shaped openings is prepared. An oversized mandrel that is approximately 25% larger than the nominal stent diameter is wrapped with an ePTFE film with a discontinuous FEP coating to a thickness of approximately 0.05 mm.

The film-mandrel assembly is placed into an oven at 320° C. for 12 minutes to bond the layers. The assembly is removed from the oven and allowed to cool at room temperature to provide an ePTFE tube. Using a $CO_2$ laser, a pattern of slits approximately 40% longer than the final inscribed circle diameter are oriented transverse to the longitudinal axis of the mandrel are cut into the tube. The tube with slits is removed from the mandrel and stretched over the nominal stent diameter mandrel and the slits open to form diamond shapes. The tube ends are temporarily fixed to length on the mandrel by ePTFE tape. The assembly is then placed into a convection oven set at 370° C. for 12 minutes. The material shrinks to form diamonds that are approximately 0.5 mm diameter inscribed circle and lattice segments are approximately 0.05 mm wide.

EXAMPLE 5

The obtained stent of Example 1 or 2 is powder coated with a thin layer of FEP powder (DuPont® FEP Fluoropolymer Resin, Product Type 5101) in a tabletop blender within which the stent is suspended. After the stent is placed within the blender with FEP powder, the blender is activated. The powder disperses into the volume of the blender chamber and the stent is powder coated. After approximately 3 seconds, the stent is removed, and is placed into a convection oven set at 320° C. for 5 minutes. After this time, the stent is removed and allowed to air cool.

The stent is then placed on a mandrel having an outer diameter approximately equal to the inner diameter of the stent. The mandrel is covered on its outer diameter with polyimide film. To temporarily fix the stent to the mandrel, the stent is placed in a convection oven set at 320° C. for 4 minutes.

After removal from the oven and cooling of the stent and mandrel assembly, a square-shaped opening lattice according to Example 3 is coaxially positioned over the stent.

The lattice is axially tensioned over the stent and comes in full contact with the outer diameter of the stent. The cover ends are temporarily fixed to length on the mandrel by ePTFE tape. A temporary layer of ePTFE film is then tightly wrapped around the assembly. The perforated cover is then placed within a convection oven set at 320° C. oven for 12 minutes to adhere the cover to the stent. After removal from the oven and being allowed to cool to ambient temperature, the temporary film wrapping is removed, and the stent and lattice covering are removed from the mandrel. The lattice is then trimmed flush with the end of the stent.

EXAMPLE 6

The obtained stent of Example 1 or 2 is powder coated as described in Example 3 above. The prepared diamond-shaped opening lattice of Example 4 is coaxially positioned over the stent. The lattice is axially tensioned over the stent, causing it to decrease in diameter and to come in full contact with the outer diameter of the stent. The lattice ends are temporarily fixed to length on the mandrel by ePTFE tape. A temporary layer of ePTFE film is then tightly wrapped around the assembly. The lattice is then placed within a convection oven set at 320° C. oven for 12 minutes. After removal from the oven and being allowed to cool to ambient temperature, the temporary film wrapping is removed, and the stent and lattice covering are removed from the mandrel. The lattice is then trimmed flush with the end of the stent.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A stent having a distal end and a proximal end and a longitudinal axis, the stent comprising:
    a first circumferential row arranged near the proximal end and extending substantially perpendicular to the longitudinal axis;
    a second circumferential row arranged near the distal end and extending substantially perpendicular to the longitudinal axis;
    a plurality of struts configured to longitudinally stabilize the stent; and
    an intermediate section extending at an angle relative to the longitudinal axis and being axially interposed between and directly connected to the first circumferential row and the second circumferential row, the intermediate section having uniform apex angles and uniform apex amplitude along a length thereof to form a uniform apex geometry the stent having an insertion configuration and a deployed configuration, the stent configured to maintain a length that is substantially constant as the stent transforms from the insertion configuration to the deployed configuration.

2. The stent of claim 1, wherein the intermediate section is a continuous series of undulations having a series of helical turns about the longitudinal axis forming one of a substantially cylindrical helical element and a tapered tubular helical element.

3. The stent of claim 2, wherein the plurality of struts including an intermediate group of struts arranged intermittently within the intermediate section of the stent to connect the helical turns.

4. The stent of claim 3, wherein the intermediate group of struts include between two and six connectors for each of the series of helical turns, and the intermediate group of struts connect adjacent rows of the series of helical turns.

5. The stent of claim 4, wherein the intermediate group of struts in a first helical row are offset from the intermediate group of struts in a second helical row, wherein the first helical row is adjacent the second helical row.

6. The stent of claim 1, wherein the plurality of struts includes a proximal group of struts directly connecting the first circumferential row to the intermediate section and a distal group of struts directly connecting the second circumferential row to the intermediate section.

7. The stent of claim 6, wherein lengths of the proximal group of struts increase along a first circumferential direction of the stent, and lengths of the distal group of struts increase along a second circumferential direction of the stent, wherein the first circumferential direction is opposite the second circumferential direction.

8. The stent of claim 6, wherein at least one of the proximal group of struts and the distal group of struts includes a notch configured to act as a hinge to facilitate bending and reduce stress around an area where the stent is deformed.

9. The stent of claim 6, further comprising a first circumferential ring including a plurality of closed cells directly connected to the first circumferential row and a second circumferential ring including a plurality of closed cells directly connected to the second circumferential row.

10. The stent of claim 1, wherein the stent includes an insertion configuration and a deployed configuration, and the stent is configured to maintain a length that is relatively constant as the stent transforms from the insertion configuration to the deployed configuration.

11. A stent having an insertion configuration and a deployed configuration, the stent comprising:
a cylindrical body configured to maintain a length that is substantially constant as the stent transforms from the insertion configuration to the deployed configuration and formed by a continuous series of rows including:
a proximal end row extending substantially perpendicular to a longitudinal axis of the cylindrical body;
a distal end row extending substantially perpendicular to the longitudinal axis of the cylindrical body; and
intermediate rows extending helically about the longitudinal axis of the cylindrical body and being axially interposed between and directly connected to the proximal end row and the distal end row, the intermediate rows having uniform apex angles and uniform apex amplitude along a length thereof.

12. The stent of claim 11, wherein the continuous series of rows includes undulations formed by struts interconnected at bends or apices.

13. The stent of claim 12, wherein the intermediate rows have a greater flexibility than at least one of the proximal end row and the distal end row.

14. The stent of claim 13, further comprising a plurality of struts connecting the bends or apices of the continuous series of rows, and each of the apices or bends of at least one of the proximal end row and the distal end row is directly connected to the apices or bends of the intermediate rows, and the apices of the intermediate rows are intermittently connected by the plurality of struts.

15. The stent of claim 11, further comprising a lattice coupled to the cylindrical body and configured to minimize or reduce the risk of introduction of emboli into a bloodstream, resist tissue encroachment into a lumen defined by the cylindrical body, and reduce pressure on a weakened part of a blood vessel to reduce the risk of vessel rupture.

16. The stent of claim 15, wherein the lattice includes openings having a series of continuous longitudinal segments that extend in a direction that is substantially parallel to the longitudinal axis of the cylindrical body.

17. A stent delivery system comprising:
a handle housing; and
a sheath configured to maintain a stent in an insertion configuration and release the stent to a deployed configuration, the stent including: a cylindrical body configured to maintain a length that is substantially constant as the stent transforms from the insertion configuration to the deployed configuration and formed by a continuous series of rows including:
a proximal end row extending substantially perpendicular to a longitudinal axis of the cylindrical body;
a distal end row extending substantially perpendicular to the longitudinal axis of the cylindrical body; and
intermediate rows extending helically about the longitudinal axis of the cylindrical body and being axially interposed between and directly connected to the proximal end row and the distal end row, the intermediate rows having uniform apex angles and uniform apex amplitude along a length thereof.

18. The stent delivery system of claim 17, wherein the sheath is configured to deliver the stent to a carotid artery of a patient.

19. The stent delivery system of claim 18, wherein the stent is configured to conform to vessel walls of the carotid artery.

20. The stent delivery system of claim 17, further comprising a thumb wheel arranged within the handle housing configured to retract the sheath to deploy the stent.

* * * * *